US009827336B2

(12) United States Patent
Bonge-Hansen et al.

(10) Patent No.: US 9,827,336 B2
(45) Date of Patent: *Nov. 28, 2017

(54) RADIO-PHARMACEUTICAL COMPLEXES

(71) Applicant: Bayer AS, Oslo (NO)

(72) Inventors: Hanne Therese Bonge-Hansen, Oslo (NO); Olav Benjamin Ryan, Oslo (NO)

(73) Assignee: BAYER AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 14/400,026

(22) PCT Filed: May 13, 2013

(86) PCT No.: PCT/EP2013/059841
§ 371 (c)(1),
(2) Date: Nov. 10, 2014

(87) PCT Pub. No.: WO2013/167756
PCT Pub. Date: Nov. 14, 2013

(65) Prior Publication Data
US 2015/0110817 A1 Apr. 23, 2015

(30) Foreign Application Priority Data

May 11, 2012 (GB) .................................. 1208309.3

(51) Int. Cl.
A61K 103/40 (2006.01)
A61K 51/10 (2006.01)
A61P 35/00 (2006.01)
A61K 51/04 (2006.01)
C07K 16/32 (2006.01)
A61K 39/00 (2006.01)

(52) U.S. Cl.
CPC ...... *A61K 51/0474* (2013.01); *A61K 51/0455* (2013.01); *A61K 51/0478* (2013.01); *A61K 51/1027* (2013.01); *A61K 51/1093* (2013.01); *C07K 16/32* (2013.01); *A61K 2039/505* (2013.01); *C07K 2317/24* (2013.01)

(58) Field of Classification Search
CPC .......... A61K 2039/505; A61K 51/0455; A61K 51/0474; A61K 51/0478; A61K 51/1027; A61K 51/1093; C07K 16/32; C07K 2317/24
See application file for complete search history.

(56) References Cited

U.S. PATENT DOCUMENTS

2010/0056787 A1 3/2010 Wadsworth et al.
2013/0183235 A1 7/2013 Ramdahl
2015/0104385 A1 4/2015 Bonge-Hansen et al.
2015/0147272 A1 5/2015 Bonge-Hansen et al.

FOREIGN PATENT DOCUMENTS

GB   WO2011/098611 A2 *  8/2011   ............. A61K 51/10
NO   WO2008/085064 A2 *  7/2008   ........... C07D 213/81
WO   WO-2006/003123 A2   1/2006
WO   WO-2008/085064 A2   7/2008
WO    WO2008085064 A2 *  7/2008
WO   WO-2011/098611 A2   8/2011
WO    WO2011098611    *  8/2011
WO   WO-2013/167754 A1  11/2013
WO   WO-2013/167755 A1  11/2013
WO   WO-2013/167756 A1  11/2013

OTHER PUBLICATIONS

International Search Report for International Patent Application No. PCT/EP2013/059841, dated Aug. 16, 2013 (5 pages).
International Preliminary Report on Patentability for International Patent Application No. PCT/EP2013/059841, dated Nov. 11, 2014 (7 pages).
Written Opinion of the International Searching Authority for International Patent Application No. PCT/EP2013/059841, dated Aug. 16, 2013 (6 pages).
International Search Report for International Patent Application No. PCT/EP2013/059840, dated Aug. 16, 2013 (5 pages).
International Preliminary Report on Patentability for International Patent Application No. PCT/EP2013/059840, dated Nov. 11, 2014 (8 pages).
Written Opinion of the International Searching Authority for International Patent Application No. PCT/EP2013/059840, dated Aug. 16, 2013 (7 pages).
International Search Report for International Patent Application No. PCT/EP2013/059839, dated Aug. 16, 2013 (5 pages).
International Preliminary Report on Patentability for International Patent Application No. PCT/EP2013/059839, dated Nov. 11, 2014 (8 pages).
Written Opinion of the International Searching Authority for International Patent Application No. PCT/EP2013/059839, dated Aug. 16, 2013 (7 pages).

* cited by examiner

Primary Examiner — Audrea Buckley
(74) Attorney, Agent, or Firm — Nixon & Vanderhye P.C.

(57) ABSTRACT

A tissue-targeting complex comprising a tissue targeting moiety, an octadentate hydroxypyridinone-containing ligand comprising four HOPO moieties and the ion of an alpha-emitting thorium radionuclide, where at least one of the four HOPO moieties is substituted at the N-position with a hydroxyalkyl solubilising group.

16 Claims, 15 Drawing Sheets

A
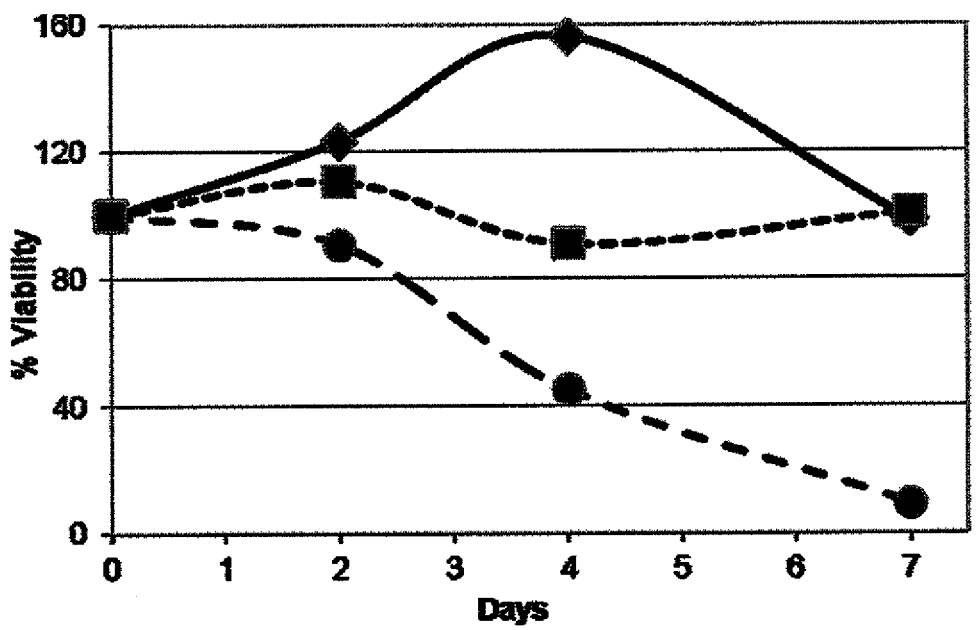
B
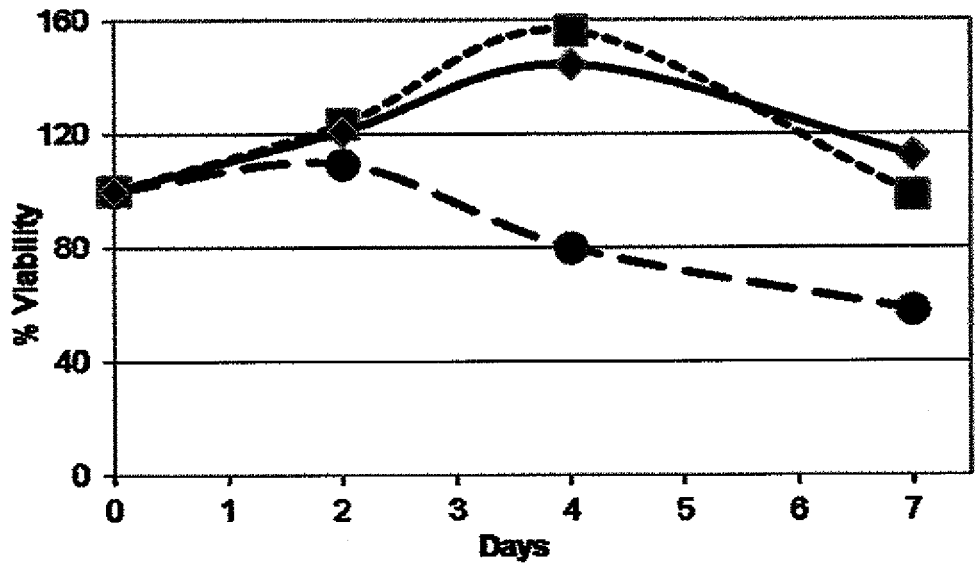
Figure 4

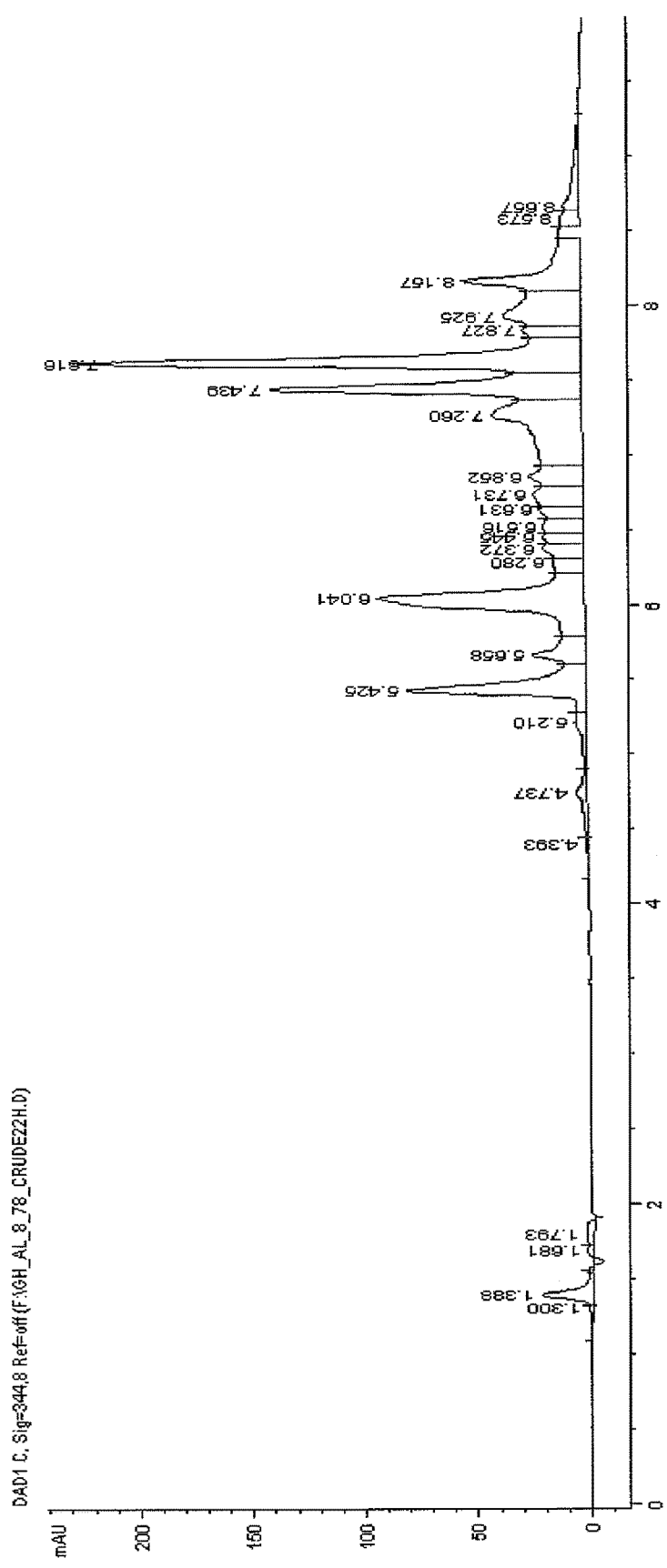
Figure 9 – HPLC analysis of the product of Example 18

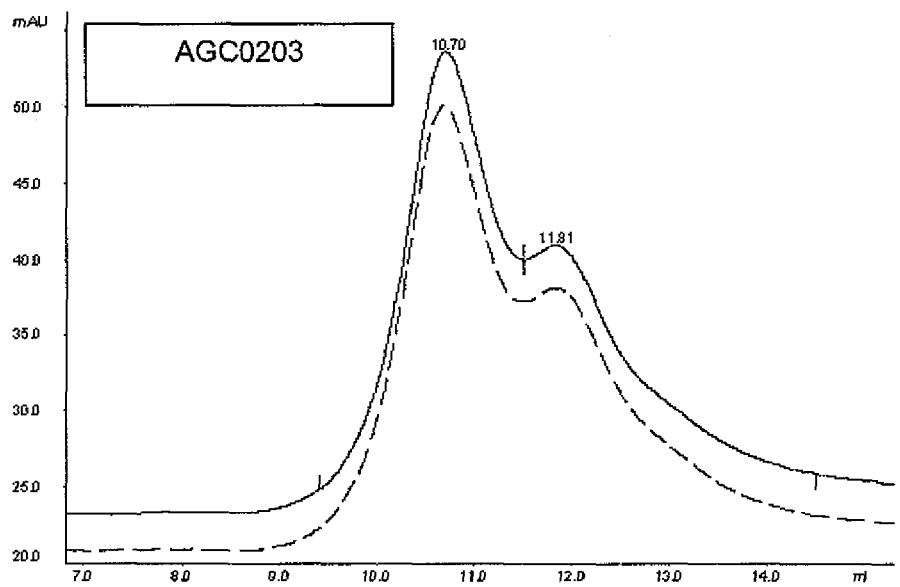
Figure 10, A
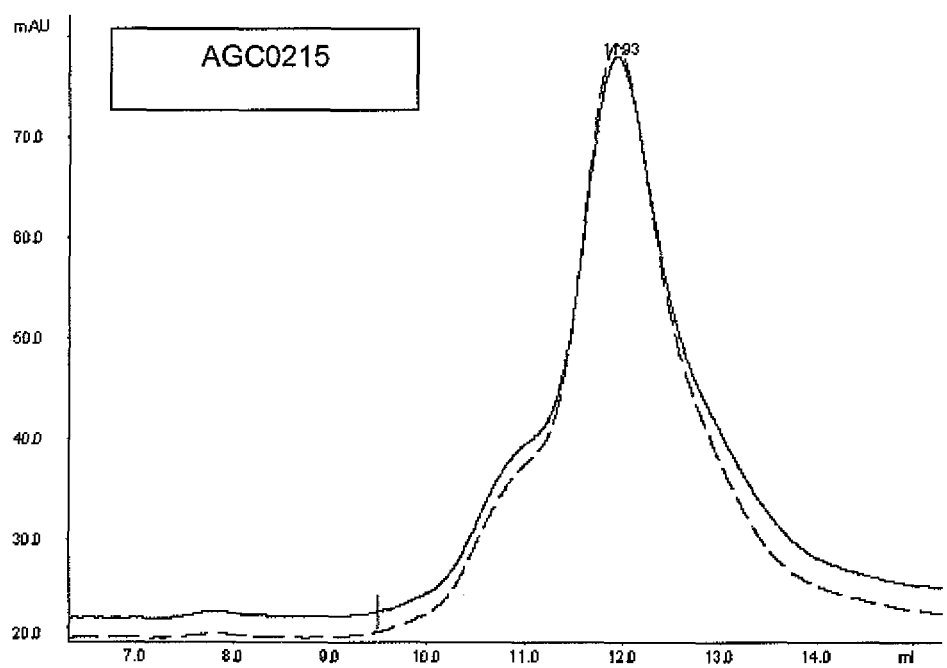
Figure 10, B

SEQUENCE LISTING

```
<160> NUMBER OF SEQ ID NOS: 10

<210> SEQ ID NO 1
<211> LENGTH: 116
<212> TYPE: PRT
<213> ORGANISM: Artificial Sequence
<220> FEATURE:
<223> OTHER INFORMATION: Back-translated from mAb HuM195, optimised and
      sub-cloned into Chinese hamster ovarian suspension cells.

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Ile
            35                  40                  45

Gly Tyr Ile Tyr Pro Tyr Asn Gly Gly Thr Gly Tyr Asn Gln Lys Phe
        50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
                100                 105                 110

Thr Val Ser Ser
        115
```

```
<210> SEQ ID NO 2
<211> LENGTH: 111
<212> TYPE: PRT
<213> ORGANISM: Artificial Sequence
<220> FEATURE:
<223> OTHER INFORMATION: Back-translated from mAb HuM195, optimised and
      sub-cloned into Chinese hamster ovarian suspension cells.

<400> SEQUENCE: 2

Asp Ile Gln Met Thr Gln Ser Pro Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys
            100                 105                 110

<210> SEQ ID NO 3
<211> LENGTH: 446
<212> TYPE: PRT
<213> ORGANISM: Artificial Sequence
<220> FEATURE:
<223> OTHER INFORMATION: Back-translated from mAb HuM195, optimised and
      sub-cloned into Chinese hamster ovarian suspension cells.

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
                195                 200                 205
Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 4
<211> LENGTH: 218
<212> TYPE: PRT
<213> ORGANISM: Artificial Sequence
<220> FEATURE:
<223> OTHER INFORMATION: Back-translated from mAb HuM195, optimised and
      sub-cloned into Chinese hamster ovarian suspension cells.

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys Arg
            100                 105                 110
```

```
Thr Val Ala Ala Pro Ser Val Phe Ile Phe Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 5
<211> LENGTH: 113
<212> TYPE: PRT
<213> ORGANISM: Artificial Sequence
<220> FEATURE:
<223> OTHER INFORMATION: Murine derived mAb

<400> SEQUENCE: 5

Asp Ile Gln Leu Thr Gln Ser Pro Ser Ser Leu Ala Val Ser Ala Gly
1               5                   10                  15

Glu Asn Val Thr Met Ser Cys Lys Ser Ser Gln Ser Val Leu Tyr Ser
            20                  25                  30

Ala Asn His Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Arg Val Gln Val Glu Asp Leu Ala Ile Tyr Tyr Cys His Gln
                85                  90                  95

Tyr Leu Ser Ser Trp Thr Phe Gly Gly Gly Thr Lys Leu Glu Ile Lys
            100                 105                 110

Arg

<210> SEQ ID NO 6
<211> LENGTH: 113
<212> TYPE: PRT
<213> ORGANISM: Artificial Sequence
<220> FEATURE:
<223> OTHER INFORMATION: Humanised version of murine derived mAb

<400> SEQUENCE: 6

Asp Ile Gln Leu Thr Gln Ser Pro Ser Ser Leu Ala Ser Ala Ala Val
1               5                   10                  15

Glu Asp Arg Thr Met Ser Cys Lys Ser Ser Gln Ser Val Leu Tyr Ser
            20                  25                  30

Ala Asn His Lys Asn Tyr Leu Ala Trp Tyr Gln Gln Lys Pro Gly Gln
        35                  40                  45

Lys Ala Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80
```

```
Ile Ser Ser Leu Gln Pro Glu Asp Ile Ala Thr Tyr Tyr Cys His Gln
                85                  90                  95

Tyr Leu Ser Ser Trp Thr Phe Gly Gly Gly Thr Lys Leu Glu Ile Lys
            100                 105                 110

Arg

<210> SEQ ID NO 7
<211> LENGTH: 116
<212> TYPE: PRT
<213> ORGANISM: Artificial Sequence
<220> FEATURE:
<223> OTHER INFORMATION: Murine derived mAb

<400> SEQUENCE: 7

Gln Val Gln Leu Gln Glu Ser Gly Ala Glu Leu Ser Lys Pro Gly Ala
1               5                   10                  15

Ser Val Lys Met Ser Cys Lys Ala Ser Gly Tyr Thr Phe Thr Ser Tyr
                20                  25                  30

Trp Leu His Trp Ile Lys Gln Arg Pro Gly Gln Gly Leu Glu Trp Ile
            35                  40                  45

Gly Tyr Ile Asn Pro Arg Asn Asp Tyr Thr Glu Tyr Asn Gln Asn Phe
50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: Humanised version of murine derived mAb

<400> SEQUENCE: 8

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Trp Leu His Trp Val Arg Gln Ala Pro Gly Gln Gly Leu Glu Trp Ile
            35                  40                  45

Gly Tyr Ile Asn Pro Arg Asn Asp Tyr Thr Glu Tyr Asn Gln Asn Phe
50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
            100                 105                 110

Thr Val Ser Ser
        115

<210> SEQ ID NO 9
<211> LENGTH: 116
```

```
<212> TYPE: PRT
<213> ORGANISM: Artificial Sequence
<220> FEATURE:
<223> OTHER INFORMATION: Humanised version of murine anti-CD22 mAb

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Trp Leu His Trp Val Arg Gln Ala Pro Gly Gln Gly Leu Glu Trp Ile
            35                  40                  45

Gly Tyr Ile Asn Pro Arg Asn Asp Tyr Thr Glu Tyr Asn Gln Asn Phe
        50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
                100                 105                 110

Thr Val Ser Ser
            115

<210> SEQ ID NO 10
<211> LENGTH: 109
<212> TYPE: PRT
<213> ORGANISM: Artificial Sequence
<220> FEATURE:
<223> OTHER INFORMATION: Affibody Fusion protein expressed in E.coli

<400> SEQUENCE: 10

Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
                20                  25                  30

Lys Leu Tyr Asp Asp Pro Ser Gln Ser Ser Glu Leu Leu Ser Glu Ala
            35                  40                  45

Lys Lys Leu Asn Asp Ser Gln Ala Pro Ser Gly Ser Gly Ser Leu Ala
        50                  55                  60

Glu Ala Lys Glu Ala Ala Asn Ala Glu Leu Asp Cys Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro Gly
                100                 105
```

RADIO-PHARMACEUTICAL COMPLEXES

FIELD OF THE INVENTION

The present invention relates to complexes of thorium isotopes and particularly with complexes of thorium-227 with certain octadentate ligands conjugated to targeting moieties. The invention also relates to the treatment of disease, particularly neoplastic diseases, involving the administration of such complexes.

BACKGROUND TO THE INVENTION

Specific cell killing can be essential for the successful treatment of a variety of diseases in mammalian subjects. Typical examples of this are in the treatment of malignant diseases such as sarcomas and carcinomas. However the selective elimination of certain cell types can also play a key role in the treatment of other diseases, especially hyperplastic and neoplastic diseases.

The most common methods of selective treatment are currently surgery, chemotherapy and external beam irradiation. Targeted radionuclide therapy is, however, a promising and developing area with the potential to deliver highly cytotoxic radiation to unwanted cell types. The most common forms of radiopharmaceutical currently authorised for use in humans employ beta-emitting and/or gamma-emitting radionuclides. There has, however, been some interest in the use of alpha-emitting radionuclides in therapy because of their potential for more specific cell killing.

The radiation range of typical alpha emitters in physiological surroundings is generally less than 100 micrometers, the equivalent of only a few cell diameters. This makes these sources well suited for the treatment of tumours, including micrometastases, because they have the range to reach neighbouring cells within a tumour but if they are well targeted then little of the radiated energy will pass beyond the target cells. Thus, not every cell need be targeted but damage to surrounding healthy tissue may be minimised (see Feinendegen et al., Radiat Res 148:195-201 (1997)). In contrast, a beta particle has a range of 1 mm or more in water (see Wilbur, Antibody Immunocon Radiopharm 4: 85-96 (1991)).

The energy of alpha-particle radiation is high in comparison with that carried by beta particles, gamma rays and X-rays, typically being 5-8 MeV, or 5 to 10 times that of a beta particle and 20 or more times the energy of a gamma ray. Thus, this deposition of a large amount of energy over a very short distance gives α-radiation an exceptionally high linear energy transfer (LET), high relative biological efficacy (RBE) and low oxygen enhancement ratio (OER) compared to gamma and beta radiation (see Hall, "Radiobiology for the radiologist", Fifth edition, Lippincott Williams & Wilkins, Philadelphia Pa., USA, 2000). This explains the exceptional cytotoxicity of alpha emitting radionuclides and also imposes stringent demands on the biological targeting of such isotopes and upon the level of control and study of alpha emitting radionuclide distribution which is necessary in order to avoid unacceptable side effects.

Table 1 below shows the physical decay properties of the alpha emitters so far broadly proposed in the literature as possibly having therapeutic efficacy.

TABLE 1

| Candidate nuclide | $T_{1/2}$* | Clinically tested for |
| --- | --- | --- |
| $^{225}$Ac | 10.0 days | leukaemia |
| $^{211}$At | 7.2 hours | glioblastoma |
| $^{213}$Bi | 46 minutes | leukaemia |
| $^{223}$Ra | 11.4 days | skeletal metastases |
| $^{224}$Ra | 3.66 days | ankylosing spondylitis |

*Half life

So far, with regards to the application in radioimmunotherapy the main attention has been focused on $^{211}$At, $^{213}$Bi and $^{225}$Ac and these three nuclides have been explored in clinical immunotherapy trials.

Several of the radionuclides which have been proposed are short-lived, i.e. have half lives of less than 12 hours. Such a short half-life makes it difficult to produce and distribute radiopharmaceuticals based upon these radionuclides in a commercial manner. Administration of a short-lived nuclide also increases the proportion of the radiation dose which will be emitted in the body before the target site is reached.

The recoil energy from alpha-emission will in many cases cause the release of daughter nuclides from the position of decay of the parent. This recoil energy is sufficient to break many daughter nuclei out from the chemical environment which may have held the parent, e.g. where the parent was complexed by a ligand such as a chelating agent. This will occur even where the daughter is chemically compatible with, i.e. complexable by, the same ligand. Equally, where the daughter nuclide is a gas, particularly a noble gas such as radon, or is chemically incompatible with the ligand, this release effect will be even greater. When daughter nuclides have half-lives of more than a few seconds, they can diffuse away into the blood system, unrestrained by the complexant which held the parent. These free radioactive daughters can then cause undesired systemic toxicity.

The use of Thorium-227 ($T_{1/2}$=18.7 days) under conditions where control of the $^{223}$Ra daughter isotope is maintained was proposed a few years ago (see WO 01/60417 and WO 02/05859). This was in situations where a carrier system is used which allows the daughter nuclides to be retained by a closed environment. In one case, the radionuclide is disposed within a liposome and the substantial size of the liposome (as compared to recoil distance) helps retain daughter nuclides within the liposome. In the second case, bone-seeking complexes of the radionuclide are used which incorporate into the bone matrix and therefore restrict release of the daughter nuclides. These are potentially highly advantageous methods, but the administration of liposomes is not desirable in some circumstances and there are many diseases of soft tissue in which the radionuclides cannot be surrounded by a mineralised matrix so as to retain the daughter isotopes.

More recently, it was established that the toxicity of the $^{223}$Ra daughter nuclei released upon decay of $^{227}$Th could be tolerated in the mammalian body to a much greater extent than would be predicted from prior tests on comparable nuclei. In the absence of the specific means of retaining the radium daughters of thorium-227 discussed above, the publicly available information regarding radium toxicity made it clear that it was not possible to use thorium-227 as a therapeutic agent since the dosages required to achieve a therapeutic effect from thorium-227 decay would result in a highly toxic and possibly lethal dosage of radiation from the decay of the radium daughters, i.e. there is no therapeutic window.

WO 04/091668 describes the unexpected finding that a therapeutic treatment window does exist in which a therapeutically effective amount of a targeted thorium-227 radionuclide can be administered to a subject (typically a mammal) without generating an amount of radium-223 sufficient to cause unacceptable myelotoxicity. This can therefore be used for treatment and prophylaxis of all types of diseases at both bony and soft-tissue sites.

In view of the above developments, it is now possible to employ alpha-emitting thorium-227 nuclei in endoradionuclide therapy without lethal myelotoxicity resulting from the generated $^{223}$Ra. Nonetheless, the therapeutic window remains relatively narrow and it is in all cases desirable to administer no more alpha-emitting radioisotope to a subject than absolutely necessary. Useful exploitation of this new therapeutic window would therefore be greatly enhanced if the alpha-emitting thorium-227 nuclei could be complexed and targeted with a high degree of reliability.

Because radionuclides are constantly decaying, the time spent handling the material between isolation and administration to the subject is of great importance. It would also be of considerable value if the alpha-emitting thorium nuclei could be complexed, targeted and/or administered in a form which was quick and convenient to prepare, preferably requiring few steps, short incubation periods and/or temperatures not irreversibly affecting the properties of the targeting entity. Furthermore, processes which can be conducted in solvents that do not need removal before administration (essentially in aqueous solution) have the considerable advantage of avoiding a solvent evaporation or dialysis step. This reduces the time and complexity of preparation, which is of key significance in the generation of radiopharmaceuticals, which decay continuously to contaminant daughter products.

In view of the need for selectivity in the delivery of cytotoxic agents in therapy, there is an evident need for targeting of alpha-radionuclide complexes. However, conjugates of suitable chelators with a small targeting peptide or small protein tend to show poor solubility in aqueous systems because the small biomolecule cannot keep the insoluble chelate in solution. Poor solubility leads to aggregation and precipitation. Aggregates are unacceptable in a drug preparation to be administered to human subjects and evidently precipitation renders a composition entirely unusable.

Furthermore, also with a larger targeting peptide/protein, such as a monoclonal antibody, the chelator will be exposed on the surface of the conjugate as a hydrophobic 'spot'. This might in some contexts lead to issues with micro aggregation.

In a biological system, such as in a human patient, hydrophobicity in general is associated with undesirable uptake in the liver. Evidently this is much more serious with highly cytotoxic agents such as alpha-emitters than for typical drug compounds. Hydrophobicity of the chelator also increases the risk of an immune response, as hydrophobicity facilitates stronger binding of antibodies produced by the host's immune system. Again this is of particular concern with alpha-emitters due to their exceptional cytotoxicity. There is thus evidently a considerable need of methods for the selective delivery of alpha-emitting thorium radionuclides by conjugates having increased hydrophilicity, particularly of the ligand portion, so as to address one or more of the issues discussed above Octadentate chelating agents containing hydroxypyridinone groups have previously been shown to be suitable for coordinating the alpha emitter thorium-277, for subsequent attachment to a targeting moiety (WO2011098611). Octadentate chelators were described, containing four 3,2-hydroxypyridinone groups joined by linker groups to an amine-based scaffold, having a separate reactive group used for conjugation to a targeting molecule. Preferred structures of the previous invention contained 3,2-hydroxypyridinone groups having a methyl substituted nitrogen in position 1 of the heterocyclic ring, and were linked to the amine based scaffold by a an amine bond involving an formic acid attached at position 4, as shown in by the compounds ALG-DD-NCS, ALG1005-38, Bb-1-HOPO-1-DEBN. In the experiment where one of these hydroxypyiridinone containing molecules was conjugated to a tumor targeting antibody, the molecule was dissolved in the organic solvent DMSO since it could not be dissolved in aqueous buffers.

The use of specific targeting moieties in cytotoxic therapy (such as cancer chemotherapy or endoradionuclide therapy) is now a well established method and numerous targets and potential targets are known. These are typically cell-surface or matrix markers (such as receptors) which are to some extent preferentially expressed in diseased cells or in cells associated with diseased cells, or in the nearby matrix. Specific binding moieties can serve to target, carry and/or bind cytotoxic elements (such as chemical toxins or radionuclides) to the vicinity of an unwanted cell type (e.g. neoplastic cells) and thereby improve the selectivity of cell killing provided by the cytotoxic agent. In order to take advantage of such specific binding property, the binding moiety must be conjugated or conjugatable to the cytotoxic agent (such as the complexed radionuclide). Many cell surface and matrix targets are known including receptors such as folate binding receptor, CD22, CD33, estrogen and progesterone receptors and many others. Typically an antibody, antibody fragment or smaller binding molecule (such as an "affibody") is generated with specificity for such a cell surface marker and conjugated to the cytotoxic agent. Any of these known methods and markers are potentially usable with radionuclide agents. However, preparation ease and time is important and for smaller binders, solubility can be critical because the conjugate as a whole must be soluble for administration.

The present inventors have now unexpectedly established that the use of a 4+ thorium-227 ion complexed by an octadentate hydroxypyridinone (HOPO)-type ligand comprising four HOPO moieties of which at least one is substituted with a suitable solubilising moiety can provide a dramatic improvement in solubility and corresponding properties of the complex.

SUMMARY OF THE INVENTION

Viewed from a first aspect the present invention therefore provides a tissue-targeting complex comprising a tissue targeting moiety, an octadentate hydroxypyridinone-containing ligand comprising four HOPO moieties and the ion of an alpha-emitting thorium radionuclide, where at least one of the four HOPO moieties is substituted at the N-position (1-position) with a hydroxyalkyl solubilising group. In one embodiment such complexes are soluble in pure water.

In a preferred embodiment, the octadentate ligand comprises at least one 3,2-HOPO moiety, and preferably 2, 3, or 4 3,2-HOPO moieties. In a further preferred embodiment, at least 2, preferably at least 3 and most preferably all 4 HOPO moieties comprise hydroxyalkyl solubilising moieties at the N-position.

Preferred targeting moieties include polyclonal and particularly monoclonal antibodies and fragments thereof. Specific binding fragments such as Fab, Fab' Fab'2 and single-chain specific binding antibodies are typical fragments.

In such complexes (and preferably in all aspects of the current invention) the thorium ion will generally be complexed by the octadentate hydroxypyridinone-containing ligand, which in turn will be attached to the tissue targeting moiety by any suitable means. Such means may include direct covalent attachment or attachment by means of any suitable specific binding pair (e.g. biotin/avidin type binding paris). Any suitable attachment may be used but direct covalent bonding or use of a covalent or binding-pair linker moiety will be typical methods. Covalent ester or amide bonds are preferred methods.

Viewed from a further aspect the invention provides the use of a tissue targeting complex comprising a tissue targeting moiety, an octadentate hydroxypyridinone-containing ligand comprising four HOPO moieties and the ion of an alpha-emitting thorium radionuclide, where at least one of the four HOPO moieties is substituted at the N-position with a hydroxyalkyl solubilising group (including any such complex described herein) in the manufacture of a medicament for the treatment of hyperplastic or neoplastic disease including any such disease described herein.

In a corresponding aspect, the invention provides a method of treatment of a human or non-human animal (particularly one in need thereof) comprising administration of at least one tissue-targeting complex comprising a tissue targeting moiety, an octadentate hydroxypyridinone-containing ligand comprising four HOPO moieties and the ion of an alpha-emitting thorium radionuclide, where at least one of the four HOPO moieties is substituted at the N-position with a hydroxyalkyl solubilising group (including any such complex described herein). Such a method is preferably for the treatment of hyperplastic or neoplastic disease including any such disease described herein. Such a method is typically carried out on a human or non-human mammalian subject, such as one in need thereof.

In a further corresponding embodiment, the invention provides for a tissue-targeting complex comprising a tissue targeting moiety, an octadentate hydroxypyridinone-containing ligand comprising four HOPO moieties and the ion of an alpha-emitting thorium radionuclide, where at least one of the four HOPO moieties is substituted at the N-position with a hydroxyalkyl solubilising group (including all such complexes as disclosed herein) for use in therapy, and in particular for use in the treatment of hyperplastic and/or neoplastic disease including any such diseases and methods described herein.

Viewed from a further aspect the invention provides a pharmaceutical composition comprising a tissue-targeting complex comprising a tissue targeting moiety, an octadentate hydroxypyridinone-containing ligand comprising four HOPO moieties and the ion of an alpha-emitting thorium radionuclide, where at least one of the four HOPO moieties is substituted at the N-position with a hydroxyalkyl solubilising group (including any such complex described herein) together with at least one pharmaceutical carrier or excipient.

So as to distinguish from thorium complexes of the most abundant naturally occurring thorium isotope, i.e. thorium-232 (half-life $10^{10}$ years and effectively non-radioactive), it should be understood that the thorium complexes and the compositions thereof claimed herein include the alpha-emitting thorium radioisotope (i.e. at least one isotope of thorium with a half-life of less than $10^3$ years, e.g. thorium-227) at greater than natural relative abundance, eg at least 20% greater. This need not affect the definition of the method of the invention where a therapeutically effective amount of a radioactive thorium, such as thorium-227 is explicitly required, but will preferably be the case in all aspects.

In all aspects of the invention, it is preferable that the alpha-emitting thorium ion is an ion of thorium-227. The 4+ ion of thorium is a preferable ion for use in the complexes of the present invention. Correspondingly, the 4+ ion of thorium-227 is highly preferred.

In a further aspect the invention furthermore provides a method for the formation of a tissue-targeting complex, said method comprising coupling a tissue targeting moiety to an octadentate hydroxypyridinone-containing ligand in aqueous solution, the complex comprising four HOPO moieties and the ion of an alpha-emitting thorium radonuclide, where at least one of the four HOPO moieties is substituted at the N-position with a hydroxyalkyl solubilising group. Such a method may be conducted in the substantial absence of any organic solvent.

Viewed from a yet still further aspect the invention also provides a kit for use in a method according to the invention, said kit comprising a tissue targeting moiety, conjugated or conjugatable to an an octadentate hydroxypyridinone-containing ligand comprising four HOPO moieties, where at least one of the four HOPO moieties is substituted at the N-position (1-position) with a hydroxyalkyl solubilising group. All binding moieties and ligands preferably being those described herein. Such a kit will optionally and preferably include an alpha-emitting thorium radionuclide, such as $^{227}$Th.

DETAILED DESCRIPTION OF THE INVENTION

In the context of the present invention, "tissue targeting" is used herein to indicate that the substance in question (particularly when in the form of a tissue-targeting complex as described herein), serves to localise itself (and particularly to localise any conjugated thorium complex) preferentially to at least one tissue site at which its presence (e.g. to deliver a radioactive decay) is desired. Thus a tissue targeting group or moiety serves to provide greater than average localisation to at least one desired site in the body of a subject following administration to that subject. The targeting moiety may, for example, bind to cell-surface markers (e.g. receptors, transport proteins, cell adhesion molecules etc) present on disease-affected cells. Similarly a tissue targeting moiety by bind to cell-surface markers (e.g. receptors, transport proteins, cell adhesion molecules etc) present on cells in the vicinity of disease affected cells. Such call-surface markers include proteins more heavily expressed on diseased cell surfaces than on healthy cell surfaces or those more heavily expressed on cell surfaces during periods of growth or replication than during dormant phases. Components present in the vicinity of target cells or tissues or associated therewith may also be utilised at the target for therapy in accordance with any aspect of the invention. For example, components present in or released into the matrix around targeted cells or tissues may be used for targeting if the presence, form or concentration allows the region to be distinguished from healthy tissue. Examples of this are matrix antigens such as tenascin, which is associated with brain tumours but is expressed in the matrix between cells. Such matrix antigens can be targeted by a single or composite targeting moiety as discussed herein.

The tissue targeting moiety may also comprise two or more components collectively having the effect of targeting the thorium complex to the desired tissue(s). This may be, for example, where one component is administered first and binds to a particular tissue, tumour or cell-type (a tissue-binding agent) and a second and/or further component (linking agent) is administered simultaneously, or preferably subsequently, which binds in vivo to the tissue-binding agent. The linking agent would be conjugated directly or indirectly to the complexed alpha-emitting thorium and thus collectively the tissue-binding and linking agents would form a tissue-targeting moiety. Suitable specific binding pairs suitable for providing the tissue binding agent and linking agent with mutual affinity are well known in the art (e.g. biotin with avidin or streptavidin).

The various aspects of the invention as described herein relate to treatment of disease, particularly for the selective targeting of diseased tissue, as well as relating to complexes, conjugates, medicaments, formulation, kits etc useful in such methods. In all aspects, the diseased tissue may reside at a single site in the body (for example in the case of a localised solid tumour) or may reside at a plurality of sites (for example where several joints are affected in arthritis or in the case of a distributed or metastasised cancerous disease).

The diseased tissue to be targeted may be at a soft tissue site, at a calcified tissue site or a plurality of sites which may all be in soft tissue, all in calcified tissue or may include at least one soft tissue site and/or at least one calcified tissue site. In one embodiment, at least one soft tissue site is targeted. The sites of targeting and the sites of origin of the disease may be the same, but alternatively may be different (such as where metastatic sites are specifically targeted). Where more than one site is involved this may include the site of origin or may be a plurality of secondary sites.

The term "soft tissue" is used herein to indicate tissues which do not have a "hard" mineralised matrix. In particular, soft tissues as used herein may be any tissues that are not skeletal tissues. Correspondingly, "soft tissue disease" as used herein indicates a disease occurring in a "soft tissue" as used herein. The invention is particularly suitable for the treatment of cancers and "soft tissue disease" thus encompasses carcinomas, sarcomas, myelomas, leukemias, lymphomas and mixed type cancers occurring in any "soft" (i.e. non-mineralised) tissue, as well as other non-cancerous diseases of such tissue. Cancerous "soft tissue disease" includes solid tumours occurring in soft tissues as well as metastatic and micro-metastatic tumours. Indeed, the soft tissue disease may comprise a primary solid tumour of soft tissue and at least one metastatic tumour of soft tissue in the same patient. Alternatively, the "soft tissue disease" may consist of only a primary tumour or only metastases with the primary tumour being a skeletal disease.

It is a key recent finding that certain alpha-radioactive thorium isotopes (e.g. $^{227}$Th) may be administered in an amount that is both therapeutically effective and does not generate intolerable myelotoxicity. As used herein, the term "acceptably non-myelotoxic" is used to indicate that, most importantly, the amount of radium-223 generated by decay of the administered thorium-227 radioisotope is generally not sufficient to be directly lethal to the subject. It will be clear to the skilled worker, however, that the amount of marrow damage (and the probability of a lethal reaction) which will be an acceptable side-effect of such treatment will vary significantly with the type of disease being treated, the goals of the treatment regimen, and the prognosis for the subject. Although the preferred subjects for the present invention are humans, other mammals, particularly dogs, will benefit from the use of the invention and the level of acceptable marrow damage may also reflect the species of the subject. The level of marrow damage acceptable will generally be greater in the treatment of malignant disease than for non-malignant disease. One well known measure of the level of myelotoxicity is the neutrophil cell count and, in the present invention, an acceptably non-myelotoxic amount of $^{223}$Ra will typically be an amount controlled such that the neutrophil fraction at its lowest point (nadir) is no less than 10% of the count prior to treatment. Preferably, the acceptably non-myelotoxic amount of $^{223}$Ra will be an amount such that the neutrophil cell fraction is at least 20% at nadir and more preferably at least 30%. A nadir neutrophil cell fraction of at least 40% is most preferred.

In addition, radioactive thorium (e.g. $^{227}$Th) containing compounds may be used in high dose regimens where the myelotoxicity of the generated radium (e.g. 223Ra) would normally be intolerable when stem cell support or a comparable recovery method is included. In such cases, the neutrophil cell count may be reduced to below 10% at nadir and exceptionally will be reduced to 5% or if necessary below 5%, providing suitable precautions are taken and subsequent stem cell support is given. Such techniques are well known in the art.

A thorium isotope of particular interest in the present invention is thorium-227, and thorium-227 is the preferred isotope for all references to thorium herein where context allows. Thorium-227 is relatively easy to produce and can be prepared indirectly from neutron irradiated $^{226}$Ra, which will contain the mother nuclide of $^{227}$Th, i.e. $^{227}$Ac ($T_{1/2}$=22 years). Actinium-227 can quite easily be separated from the $^{226}$Ra target and used as a generator for $^{227}$Th. This process can be scaled to industrial scale if necessary, and hence the supply problem seen with most other alpha-emitters considered candidates for molecular targeted radiotherapy can be avoided.

Thorium-227 decays via radium-223. In this case the primary daughter has a half-life of 11.4 days. From a pure $^{227}$Th source, only moderate amounts of radium are produced during the first few days. However, the potential toxicity of $^{223}$Ra is higher than that of $^{227}$Th since the emission from $^{223}$Ra of an alpha particle is followed within minutes by three further alpha particles from the short-lived daughters (see Table 2 below which sets out the decay series for thorium-227).

TABLE 2

| Nuclide | Decay mode | Mean particle energy (MeV) | Half-life |
|---|---|---|---|
| $^{227}$Th | α | 6.02 | 18.72 days |
| $^{223}$Ra | α | 5.78 | 11.43 days |
| $^{219}$Rn | α | 6.88 | 3.96 seconds |
| $^{215}$Po | α | 7.53 | 1.78 ms |
| $^{211}$Pb | β | 0.45 | 36.1 minutes |
| $^{211}$Bi | α | 6.67 | 2.17 minutes |
| $^{207}$Tl | β | 1.42 | 4.77 minutes |
| $^{207}$Pb | | | Stable |

Partly because it generates potentially harmful decay products, thorium-227 ($T_{1/2}$=18.7 days) has not been widely considered for alpha particle therapy.

Thorium-227 may be administered in amounts sufficient to provide desirable therapeutic effects without generating so much radium-223 as to cause intolerable bone marrow suppression. It is desirable to maintain the daughter isotopes in the targeted region so that further therapeutic effects may be derived from their decay. However, it is not necessary to maintain control of the thorium decay products in order to have a useful therapeutic effect without inducing unacceptable myelotoxicity.

Assuming the tumour cell killing effect will be mainly from thorium-227 and not from its daughters, the likely therapeutic dose of this isotope can be established by comparison with other alpha emitters. For example, for astatine-211, therapeutic doses in animals have been typically 2-10 MBq per kg. By correcting for half-life and energy the corresponding dosage for thorium-227 would be at least 36-200 kBq per kg of bodyweight. This would set a lower limit on the amount of $^{227}$Th that could usefully be administered in expectation of a therapeutic effect. This calculation assumes comparable retention of astatine and thorium. Clearly however the 18.7 day half-life of the thorium will most likely result in greater elimination of this isotope before its decay. This calculated dosage should therefore normally be considered to be the minimum effective amount. The therapeutic dose expressed in terms of fully retained $^{227}$Th (i.e. $^{227}$Th which is not eliminated from the body) will typically be at least 18 or 25 kBq/kg, preferably at least 36 kBq/kg and more preferably at least 75 kBq/kg, for example 100 kBq/kg or more. Greater amounts of thorium would be expected to have greater therapeutic effect but cannot be administered if intolerable side effects will result. Equally, if the thorium is administered in a form having a short biological half-life (i.e. the half life before elimination from the body still carrying the thorium), then greater amounts of the radioisotope will be required for a therapeutic effect because much of the thorium will be eliminated before it decays. There will, however, be a corresponding decrease in the amount of radium-223 generated. The above amounts of thorium-227 to be administered when the isotope is fully retained may easily be related to equivalent doses with shorter biological half-lives. Such calculations are well known in the art and given in WO 04/091668 (e.g. in the text an in Examples 1 and 2).

If a radiolabelled compound releases daughter nuclides, it is important to know the fate, if applicable, of any radioactive daughter nuclide(s). With $^{227}$Th, the main daughter product is $^{223}$Ra, which is under clinical evaluation because of its bone seeking properties. Radium-223 clears blood very rapidly and is either concentrated in the skeleton or excreted via intestinal and renal routes (see Larsen, J Nucl Med 43(5, Supplement): 160P (2002)). Radium-223 released in vivo from $^{227}$Th may therefore not affect healthy soft tissue to a great extent. In the study by Müller in Int. J. Radiat. Biol. 20:233-243 (1971) on the distribution of $^{227}$Th as the dissolved citrate salt, it was found that $^{223}$Ra generated from $^{227}$Th in soft tissues was readily redistributed to bone or was excreted. The known toxicity of alpha emitting radium, particularly to the bone marrow, is thus an issue with thorium dosages.

It was established for the first time in WO 04/091668 that, in fact, a dose of at least 200 kBq/kg of $^{223}$Ra can be administered and tolerated in human subjects. These data are presented in that publication. Therefore, it can now be seen that, quite unexpectedly, a therapeutic window does exist in which a therapeutically effective amount of $^{227}$Th (such as greater than 36 kBq/kg) can be administered to a mammalian subject without the expectation that such a subject will suffer an unacceptable risk of serious or even lethal myelotoxicity. Nonetheless, it is extremely important that the best use of this therapeutic window be made and therefore it is essential that the radioactive thorium be quickly and efficiently complexed, and held with very high affinity so that the greatest possible proportion of the dose is delivered to the target site.

The amount of $^{223}$Ra generated from a $^{227}$Th pharmaceutical will depend on the biological half-life of the radiolabeled compound. The ideal situation would be to use a complex with a rapid tumor uptake, including internalization into tumor cell, strong tumor retention and a short biological half-life in normal tissues. Complexes with less than ideal biological half-life can however be useful as long as the dose of $^{223}$Ra is maintained within the tolerable level. The amount of radium-223 generated in vivo will be a factor of the amount of thorium administered and the biological retention time of the thorium complex. The amount of radium-223 generated in any particular case can be easily calculated by one of ordinary skill. The maximum administrable amount of $^{227}$Th will be determined by the amount of radium generated in vivo and must be less than the amount that will produce an intolerable level of side effects, particularly myelotoxicity. This amount will generally be less than 300 kBq/kg, particularly less than 200 kBq/kg and more preferably less than 170 kBq/kg (e.g less than 130 kBq/kg). The minimum effective dose will be determined by the cytotoxicity of the thorium, the susceptibility of the diseased tissue to generated alpha irradiation and the degree to which the thorium is efficiently combined, held and delivered by the targeting complex (being the combination of the ligand and the targeting moiety in this case).

In the method of invention, the thorium complex is desirably administered at a thorium-227 dosage of 18 to 400 kBq/kg bodyweight, preferably 36 to 200 kBq/kg, (such as 50 to 200 kBq/kg) more preferably 75 to 170 kBq/kg, especially 100 to 130 kBq/kg. Correspondingly, a single dosage until may comprise around any of these ranges multiplied by a suitable bodyweight, such as 30 to 150 Kg, preferably 40 to 100 Kg (e.g. a range of 540 kBq to 4000 KBq per dose etc). The thorium dosage, the complexing agent and the administration route will moreover desirably be such that the radium-223 dosage generated in vivo is less than 300 kBq/kg, more preferably less than 200 kBq/kg, still more preferably less than 150 kBq/kg, especially less than 100 kBq/kg. Again, this will provide an exposure to $^{223}$Ra indicated by multiplying these ranges by any of the bodyweights indicated. The above dose levels are preferably the fully retained dose of $^{227}$Th but may be the administered dose taking into account that some $^{227}$Th will be cleared from the body before it decays.

Where the biological half-life of the $^{227}$Th complex is short compared to the physical half-life (e.g. less than 7 days, especially less than 3 days) significantly larger administered doses may be needed to provide the equivalent retained dose. Thus, for example, a fully retained dose of 150 kBq/kg is equivalent to a complex with a 5 day half-life administered at a dose of 711 kBq/kg. The equivalent administered dose for any appropriate retained doses may be calculated from the biological clearance rate of the complex using methods well known in the art.

Since the decay of one $^{227}$Th nucleus provides one $^{223}$Ra atom, the retention and therapeutic activity of the $^{227}$Th will be directly related to the $^{223}$Ra dose suffered by the patient. The amount of $^{223}$Ra generated in any particular situation can be calculated using well known methods.

In a preferred embodiment, the present invention therefore provides a method for the treatment of disease in a mammalian subject (as described herein), said method comprising administering to said subject a therapeutically effective quantity of a conjugate comprising a tissue targeting moiety, an octadentate ligand (especially any of those described herein) and a radioactive thorium isotope (e.g. thorium-227).

It is obviously desirable to minimise the exposure of a subject to the $^{223}$Ra daughter isotope, unless the properties of this are usefully employed. In particular, the amount of radium-223 generated in vivo will typically be greater than 40 kBq/kg, e.g. greater than 60 kBq/Kg. In some cases it will be necessary for the $^{223}$Ra generated in vivo to be more than 80 kBq/kg, e.g. greater than 100 or 115 kBq/kg.

Thorium-227 labelled conjugates in appropriate carrier solutions may be administered intravenously, intracavitary (e.g. intraperitoneally), subcutaneously, orally or topically, as a single application or in a fractionated application regimen. Preferably the complexes conjugated to a targeting moiety will be administered as solutions by a parenteral (e.g. transcutaneous) route, especially intravenously or by an intracavitary route. Preferably, the compositions of the present invention will be formulated in sterile solution for parenteral administration.

Thorium-227 in the methods and products of the present invention can be used alone or in combination with other treatment modalities including surgery, external beam radiation therapy, chemotherapy, other radionuclides, or tissue temperature adjustment etc. This forms a further, preferred embodiment of the method of the invention and formulations/medicaments may correspondingly comprise at least one additional therapeutically active agent such as another radioactive agent or a chemotherapeutic agent.

In one particularly preferred embodiment the subject is also subjected to stem cell treatment and/or other supportive therapy to reduce the effects of radium-223 induced myelotoxicity.

According to this invention $^{227}$Th may be complexed by targeting complexing agents. Typically the targeting moieties will have a molecular weight from 100 g/mol to several million g/mol (particularly 100 g/mol to 1 million g/mol), and will preferably have affinity for a disease-related receptor either directly, and/or will comprise a suitable pre-administered binder (e.g. biotin or avidin) bound to a molecule that has been targeted to the disease in advance of administering $^{227}$Th. Suitable targeting moieties include poly- and oligo-peptides, proteins, DNA and RNA fragments, aptamers etc, preferably a protein, e.g. avidin, strepatavidin, a polyclonal or monoclonal antibody (including IgG and IgM type antibodies), or a mixture of proteins or fragments or constructs of protein. Antibodies, antibody constructs, fragments of antibodies (e.g. FAB fragments or any fragment comprising at least one antigen binding region(s)), constructs of fragments (e.g. single chain antibodies) or a mixture thereof are particularly preferred. Suitable fragments particularly include Fab, F(ab')$_2$, Fab' and/or scFv. Antibody constructs may be of any antibody or fragment indicated herein.

In one embodiment, the targeting moiety may have specificity for a cell surface receptor such as CD22, CD33, folate receptor, estrogen and/or progesterone receptors or any cell surface receptor associated with neoplastic cell types.

In an alternative embodiment, the targeting moiety does not have specificity for CD22 or CD33. In one embodiment the targeting moiety does not bind receptor CD22 and/or does not bind receptor CD33. Not binding may be taken as binding to a degree no greater than the binding to a control receptor such as insulin receptor.

In a further embodiment, the specific binding moiety may be an "antibody mimetic" such as a peptide binder with at least one specific binding region analogous to that of an antibody and with molecular mass below around 10 kD (e.g. 8 kD or less, such as 0.5 to 7 kD). Such specific binders may be peptides composed of, for example, 20 to 100 amino acids, preferably 35 to 80 amino acids (e.g. around 45 to around 70 amino acids). Well known specific binders of this sort include Affibody molecules which consist of around 55-60 amino acids with a molecular weight around 5-7 kD. An Affibody containing fusion protein is exemplified herein. Such binders form one preferred embodiment. For comparison, the mass of a typical antibody is around 150 kDa, and a single-domain antibody fragment (scFv) is around 12-15 kDa.

Also suitable for use in the present invention are therapeutic conjugates of complexed $^{227}$Th with a peptide, amino acid, steroidal or non-steroidal hormone, folate, estrogen, testosterone, biotin, or other specific-binding compounds with molecular weight typically below 10 000 g/mol.

Generally, the octadentate ligand is conjugated directly or indirectly (e.g. via a linker moiety) to the targeting moiety. General constructs of this type; i.e. of active (e.g. therapeutically or diagnostically active) metal—complexing moiety—optional linker moiety—targeting moiety, are well known in the fields of targeted radiopharmaceuticals and targeted imaging agents. However, little or no work is available assessing the suitability of various ligands for specific use with thorium 4+ ions. In this regard reference may be had for example to "Handbook of Targeted Delivery of Imaging Agents", Ed. Torchilin, CRC Press, 1995.

The most relevant previous work on thorium ions with hydroxypyridinone ligands was published as WO2011/098611 and discloses the relative ease of generation of thoruim ions complexed with octadentate HOPO-containing ligands.

Previously known chelators for thorium also include the polyaminopolyacid chelators which comprise a linear, cyclic or branched polyazaalkane backbone with acidic (e.g. carboxyalkyl) groups attached at backbone nitrogens. Examples of such chelators include DOTA derivatives such as p-isothiocyanatobenzyl-1,4,7,10-tetraazacyclododecane-1,4,7,10-tetraacetic acid (p-SCN-Bz-DOTA) and DTPA derivatives such as p-isothiocyanatobenzyl-diethylenetriaminepentaacetic acid (p-SCN-Bz-DTPA), the first being cyclic chelators, the latter linear chelators.

Derivatives of 1,4,7,10-tetraazacyclododecane-1,4,7,10-tetraacetic acid have been previously exemplified, but standard methods cannot easily be used to chelate thorium with DOTA derivatives. Heating of the DOTA derivative with the metal provides the chelate effectively, but often in low yields. There is a tendency for at least a portion of the ligand to irreversibly denature during the procedure. Furthermore, because of its relatively high susceptibility to irreversible denaturation, it is generally necessary to avoid attachment of the targeting moiety until all heating steps are completed. This adds an extra chemical step (with all necessary work-up and separation) which must be carried out during the decay lifetime of the alpha-emitting thorium isotope. Obviously it is preferable not to handle alpha-emitting material in this way or to generate corresponding waste to a greater extent than necessary. Furthermore, all time spend preparing the conjugate wastes a proportion of the thorium which will decay during this preparatory period.

It is preferred that the complexes of alpha-emitting thorium and an octadentate ligand in all aspects of the present invention are formed or formable without heating above 60° C. (e.g. without heating above 50° C.), preferably without heating above 38° C. and most preferably without heating above 25° C.

It is additionally preferred that the conjugate of the targeting moiety and the octadentate ligand be prepared prior to addition of the alpha-emitting thorium isotope (e.g. $^{227}$Th$^{4+}$ ion).) The products of the invention are thus preferably formed or formable by complexation of alpha-emitting thorium isotope (e.g. $^{227}$Th$^{4+}$ ion) by a conjugate of an octadentate ligand and a tissue-targeting moiety.

The chelators may be non-phosphonate molecules and in one embodiment of the present invention the $^{227}$Th will not be attached to any phosphonate or other bone-targeting group nor administered with such materials.

The present inventors have now established that complexes comprising octadentate hydroxypyridinone-containing ligand comprising four HOPO moieties and the ion of an alpha-emitting thorium radionuclide are highly amenable to generation at room temperature and/or physiological temperature (e.g. at 20° C. or 37° C.). Such complexes may be generated rapidly and furthermore since the temperature of generation is comparatively low the complexation of the thorium component may take place after the ligand moiety has been bound or otherwise conjugated to the tissue-targeting moiety, thus reducing the number of steps required after addition of the radioisotope.

In addition to the above, the more water soluble nature of the octadentate hydroxypyridinone-containing ligand comprising four HOPO moieties wherein at least one HOPO moiety comprises a hydroxyalkyl solubilising group serves to further improve the ease of manufacture of the complete conjugate. Specifically, during manufacturing of the conjugate a hydrophobic chelator, such as a previously known octadentate ligand, has to be dissolved in an organic solvent, such as DMSO or DMA. Removal of all traces of the organic solvent after conjugation is necessary but difficult with such non-volatile polar organic solvents and complete removal is difficult to prove analytically. Time spent in analysis is obviously undesirable where an alpha-emitter has been incorporated because the radionuclide continues to decay and the potency of the conjugate reduces with time.

Due to the requirement for an organic solvent, a hydrophobic chelator is challenging to combine not only with proteinaceous targeting molecules but even more so with alternative targeting molecules that are more hydrophilic, including nanoparticles having PEG or dextrane on the surface.

A PEG or alternative hydrophilic highly water soluble spacer may be desired for biological reasons, such as prolonged halflife or reducing an immune response. The manufacturing of the chelator—PEG unit prior to conjugation to the protein is also challenging due to the difference in solubility properties of the two parts. A PEG, or similar, spacer introduces more hydrophilicity into the molecule, between the chelating moiety and the carrier protein. However, this only moves the chelator further away from the carrier protein, while the hydrophobicity of the chelator is not affected. Therefore a hydrophobic chelator may still be recognized as a hydrophobic spot on the surface of the (PEGylated) targeting molecule and generate undesirable reactions as discussed herein above.

Various types of targeting compounds that may be linked to thorium (e.g. thorium-227) via an octadentate chelator (comprising a coupling moiety as described herein). The targeting moiety may be selected from known targeting groups, which include monoclonal or polyclonal antibodies, growth factors, peptides, hormones and hormone analogues, folate and folate derivatives, botin, avidin and streptavidin or analogues thereof. Other possible targeting groups include RNA, DNA, or fragments thereof (such as aptamer), oligonucleotides, carbohydrates, lipids or compounds made by combining such groups with or without proteins etc. PEG moieties may be included as indicated above, such as to increase the biological retention time and/or reduce the immune stimulation.

The tissue targeting moiety may, in one embodiment, exclude bone-seekers, liposomes and folate conjugated antibodies or antibody fragments. Alternatively, such moieties may be included.

The thorium (e.g. thorium-227) labelled molecules of the invention may be used for the treatment of cancerous or non-cancerous diseases by targeting disease-related receptors. Typically, such a medical use of $^{227}$Th will be by radioimmunotherapy based on linking $^{227}$Th by a chelator to an antibody, an antibody fragment, or a construct of antibody or antibody fragments for the treatment of cancerous or non-cancerous diseases. The use of $^{227}$Th in methods and pharmaceuticals according to the present invention is particularly suitable for the treatment of any form of cancer including carcinomas, sarcomas, lymphomas and leukemias, especially cancer of the lung, breast, prostate, bladder, kidney, stomach, pancreas, oesophagus, brain, ovary, uterus, oral cancer, colorectal cancer, melanoma, multiple myeloma and non-Hodgkin's lymphoma.

The amount of $^{223}$Ra released could be diminished if the molecule carrying $^{227}$Th has a short biological retention half-time in vivo because the radionuclide will mostly be eliminated before a high proportion of the $^{227}$Th has decayed to $^{223}$Ra. The amount of $^{227}$Th would, however, need to be increased in order to remain therapeutically effective, according to the present invention. If the complexing agent is selected so as to deliver the $^{227}$Th into the interior of the targeted cells, this will further increase the specific cytotoxicity and reduce the systemic toxic effect of the radioactive daughters because of at least partial retention of daughter isotopes at the tumour site. Both of these features widen the $^{227}$Th therapeutic window and thus form preferred embodiments of the invention.

In a further embodiment of the invention, patients with both soft tissue and skeletal disease may be treated both by the $^{227}$Th and by the $^{223}$Ra generated in vivo by the administered thorium. In this particularly advantageous aspect, an extra therapeutic component to the treatment is derived from the acceptably non-myelotoxic amount of $^{223}$Ra by the targeting of the skeletal disease. In this therapeutic method, $^{227}$Th is typically utilised to treat primary and/or metastatic cancer of soft tissue by suitable targeting thereto and the $^{223}$Ra generated from the $^{227}$Th decay is utilised to treat related skeletal disease in the same subject. This skeletal disease may be metastases to the skeleton resulting from a primary soft-tissue cancer, or may be the primary disease where the soft-tissue treatment is to counter a metastatic cancer. Occasionally the soft tissue and skeletal diseases may be unrelated (e.g. the additional treatment of a skeletal disease in a patient with a rheumatological soft-tissue disease).

A key aspect of the present invention in all respects is the use of an octadentate ligand, particularly an octadentate hydroxypyridinone-containing ligand comprising four HOPO moieties. Such ligands will typically comprise at least four chelating groups each independently having the following substituted pyridine structure (I):

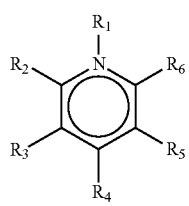

Wherein $R_1$ is an optional N-substituent solubilising group which will be present in at least one of the four moieties of formula I and may be present in 2, 3 or all 4 such moieties. $R_1$ may thus be absent or may be selected from OH and hydroxyalkyl moieties. Suitable hydroxyalkyl moieties will comprise at least one OH group but may optionally comprise more than one, such as two, three or four OH groups. One or two OH groups are most preferred on the hydroxyalkyl moiety.

The nitrogen on the pyridinone ring of HOPO moiety (especially the 3,2-HOPO and 2,3-HOPO) is a suitable point for introducing hydrophilic substituents without grossly affecting the properties of the ring, and importantly, which will face outwards after conjugating the molecule to a carrier protein or other targeting molecule. We have previously shown that a chelator based on a pyrimidone ring having a methyl group in this position is suitable for chelation of thorium ions. The novel chelators have alternative groups introduced, including a hydroxyethyl at the N-position. Surprisingly, the minor change from methyl to hydroxylethyl resulted in a chelator which was completely soluble in pure water. This molecule and some related examples are shown below.

As used herein, all hydrocarbyl moieties are independently selected from short hydrocarbyl groups, such as C1 to C8 hydrocarbyl, including C1 to C8 alkyl, alkenyl or alkynyl groups. Correspondingly, alkyl groups will typically be straight or branched chain C1 to C8 alkyl groups such as methyl, ethyl, n- or iso-propy, n-, iso- or sec-butyl and so forth.

Highly preferred $R_1$ groups include straight or branched chain alkyl groups (such as those indicated above) having one, two or more hydroxy groups attached to a carbon atom of the alkyl chain. Some highly preferred hydroxyalkyl groups include hydroxymethyl, hydroxyethyl, hydroxy n-propyl, hydroxy iso-propyl, di-hydroxy n-propyl (e.g. 1,2-, 2,3- or 1,3-di-hydroxy propyl), hydroxy n-butyl, di-hydroxy n-butyl and tri-hydroxy n-butyl with hydroxyethyl being most highly preferred. In one embodiment, each of the 4 HOPO moieties of the octadentate ligand will comprise a hydroxylakyl (such as hydroxyethyl) group at position $R_1$. In a further embodiment, all four HOPO moieties will comprise the same hydroxyalkyl group (e.g. all 4 HOPO groups will be N-substituted with hydroxyethyl or all 4 will be substituted with di-hydroxy propyl).

In a highly preferred embodiment, all 4 HOPO groups will be the same HOPO group selected from 3,2 HOPO and 2,3, HOPO groups. In a further highly preferred embodiment (which may optionally be combined with the previous), all four HOPO groups will be N-substituted with the same hydroxyalkly group selected from hydroxymethyl, hydroxyethyl, hydroxy propyl, hydroxybutyl, dihydroxypropyl and dihydroxybutyl. Of this list hydroxyethyl, hydroxypropyl and dihydroxypropyl are most preferred.

In Formula I, groups $R_2$ to $R_6$ may each independently be selected from H, OH, =O, short hydrocarbyl (as described herein), a linker moiety (as described herein) and/or a coupling moiety (as described herein). Generally, at least one of groups $R_2$ to $R_6$ will be OH. Generally, at least one of groups $R_2$ to $R_6$ will be =O. Generally, at least one of groups $R_2$ to $R_6$ will be a linker moiety (as described herein). Preferably, exactly one of groups $R_2$ to $R_6$ will be =O. Preferably exactly one of groups $R_2$ to $R_6$ will be OH. Preferably exactly one of groups $R_2$ to $R_6$ will be a linker moiety (as described herein). The remaining groups $R_2$ to $R_6$ may be any of those moieties indicated herein, but are preferably H. Where a linker moiety or any additional linker, template or chelating groups attached to a linker moiety do not comprise a coupling moiety then one of groups $R_1$ to $R_6$ is preferably a coupling moiety (as described herein).

In a preferred embodiment, one of groups $R_2$ to $R_6$ will be OH and one of $R_2$ to $R_6$ will be =O and the OH and =O groups will be on neighbouring atoms of the ring. Thus, in a preferred embodiment, OH and =O may be on atoms 2,3; 3,2; 3,4; or 4,3 respectively (numbering from the nitrogen as would be expected). Octadentate ligands having at least one chelating moiety wherein OH and =O groups are present at positions 3 and 2 respectively are highly preferred. The octadentate ligands may have 2, 3 or 4 such chelating groups, where 2 or 4 such groups are highly preferred. N-substituted 3,2-HOPO moieties are highly preferred as all four complexing moieties of the octadentate ligand.

Suitable chelating moieties may be formed by methods known in the art, including the methods described in U.S. Pat. No. 5,624,901 (e.g. examples 1 and 2) and WO2008/063721 (both incorporated herein by reference).

As used herein, the term "linker moiety" ($R_L$ in formula II) is used to indicate a chemical entity which serves to join at least two chelating groups in the octadentate ligands, which form a key component in various aspects of the invention. Typically, each chelating group (e.g. those of formula I above and/or formula II below) will be bi-dentate and so four chelating groups, of which at least one is of formula I, will typically be present in the ligand. Such chelating groups are joined to each other by means of their linker moieties. Thus, a linker moiety (e.g. group $R_L$ below) may be shared between more than one chelating group of formula I and/or II. The linker moieties may also serve as the point of attachment between the complexing part of the octadentate ligand and the targeting moiety. In such a case, at least one linker moiety will join to a coupling moiety ($R_C$). Suitable linker moieties include short hydrocarbyl groups, such as C1 to C12 hydrocarbyl, including C1 to C12 alkyl, alkenyl or alkynyl group, including methyl, ethyl, propyl, butyl, pentyl and/or hexyl groups of all topologies.

Linker moieties may also be or comprise any other suitably robust chemical linkages including esters, ethers, amine and/or amide groups. The total number of atoms joining two chelating moieties (counting by the shortest path if more than one path exists) will generally be limited, so as to constrain the chelating moieties in a suitable arrangement for complex formation. Thus, linker moieties will typically be chosen to provide no more than 15 atoms between chelating moieties, preferably, 1 to 12 atoms, and more preferably 1 to 10 atoms between chelating moieties. Where a linker moiety joins two chelating moieties directly, the linker will typically be 1 to 12 atoms in length, preferably 2 to 10 (such as ethyl, propyl, n-butyl etc). Where the linker moiety joins to a central template (see below) then each linker may be shorter with two separate linkers joining the chelating moieties. A linker length of 1 to 8 atoms, preferably 1 to 6 atoms may be preferred in this case (methyl, ethyl and propyl being suitable, as are groups such as these having an ester, ether or amide linkage at one end or both).

In addition to the linker moiety, which primarily serves to link the various chelating groups of the octadentate ligand to each other and/or to a central template, the octadentate preferably further comprises a "coupling moiety" ($R_C$). The function of the coupling moiety is to link the octadentate ligand to the targeting moiety. This may be achieved by either covalent or non-covalent attachment (e.g. by a specific binding pair such as biotin/avidin (streptavidin). Linker moieties as described above form possible coupling moieties. Preferably coupling moieties will be covalently linked to the chelating groups, either by direct covalent attachment to one of the chelating groups or more typically by attachment to a linker moiety or template. Should two or more coupling moieties be used, each can be attached to any of the available sites such as on any template, linker or chelating group.

In one embodiment, the coupling moiety may have the structure:

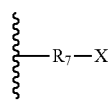

wherein $R_7$ is a bridging moiety, which is a member selected from substituted or unsubstituted alkyl, substituted or unsubstituted heteroalkyl, substituted or unsubstituted heterocycloalkyl, substituted or unsubstituted aryl and substituted or unsubstituted heteroaryl; and X is a targeting moiety or a reactive functional group. The preferred bridging moieties include all those groups indicated herein as suitable linker moieties. Preferred targeting moieties include all of those described herein and preferred reactive X groups include any group capable of forming a covalent linkage to a targeting moiety, including, for example, COOH, OH, SH, NHR and COH groups, where the R of NHR may be H or any of the short hydrocarbyl groups described herein. Highly preferred groups for attachment onto the targeting moiety include epsilon-amines of lysine residues and thiol groups of cysteine residues.

Non-limiting examples of suitable reactive X groups, include N-hydroxysuccimidylesters, imidoesters, acylhalides, N-maleimides, alpha-halo acetyl and isothiocyanates, where the latter three are suitable for reaction with a thiol group.

The coupling moiety is preferably attached, so that the resulting coupled octadentate ligand will be able to undergo formation of stable metal ion complexes. The coupling moiety will thus preferably link to the linker, template or chelating moiety at a site which does not significantly interfere with the complexation. Such a site will preferably be on the linker or template, more preferably at a position distant from the surface binding to the target.

Preferred chelating groups include those of formula II below:

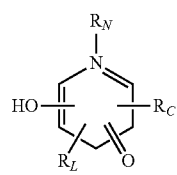

II

In the above formula II, the =O moiety represents a keto-group attached to any carbon of the pyridine ring, the —OH represents a hydroxy moiety attached to any carbon of the pyridine ring and the —$R_L$ represents a linker moiety which attaches the hydroxypyridinone moiety to other complexing moieties so as to form the overall octadentate ligand. Any linker moiety described herein is suitable as $R_L$ including short hydrocarbyl groups, such as C1 to C8 hydrocarbyl, including C1 to C8 alkyl, alkenyl or alkynyl group, including methyl, ethyl, propyl, butyl, pentyl and/or hexyl groups of all topologies. $R_L$ may join the ring of formula II at any carbon of the pyridine ring. The $R_L$ groups may then in turn bond directly to another chelating moiety, to another linker group and/or to a central atom or group, such as a ring or other template (as described herein). The linkers, chelating groups and optional template moieties are selected so as to form an appropriate octadentate ligand.

In one preferred embodiment the —OH and =O moieties of formula II reside on neighbouring atoms of the pyridine ring, such that 2,3-, 3,2-; 4,3-; and 3,4-hydroxypyridinone derivatives are all highly suitable.

Moiety $R_L$ resides on the nitrogen of the pyridine ring. Group $R_N$ may be absent in some groups of formula II where more than one different group of formula II is present in the octadentate ligand. However, at least one $R_N$ group in each octadentate ligand will be a hydroxyalkyl group as indicated herein.

In one preferred embodiment, at least one 3,2-hydroxypyridinone moiety is present in the octadentate ligand structure. This may evidently be substituted by any of the various substituent moieties indicated herein.

Since each of the moieties of formula II has two potentially complexing oxygens, one embodiment of the present invention provides for an octadentate ligand comprising at least 2, preferably at least 3 and most preferably 4 independently chosen moieties of formula II. Each moiety of formula II may have an independent substitution pattern, but in one preferred embodiment, at least one moiety is a 3,2-hydroxypyridinone moiety. The ligand may include 2, 3 or 4 3,2-hydroxypyridinone moieties (substituted as appropriate, as described herein).

Each moiety of formula I or II in the octadentate ligand may be joined to the remainder of the ligand by any appropriate linker group as discussed herein and in any appropriate topology. For example, four groups of formula I may be joined by their linker groups to a backbone so as to form a linear ligand, or may be bridged by linker groups to form a "oligomer" type structure, which may be linear or cyclic. Alternatively, the ligand moieties of formulae I and/or II may be joined in a "cross" or "star" topography to a central atom or group, each by a linker (e.g. "$R_L$" moiety). Linker ($R_L$) moieties may join solely through carbon-carbon bonds, or may attach to each other, to other chelating groups, to a backbone, template, coupling moiety or other linker by any appropriately robust functionality including an amine, amide, ester, ether, thio-ether or disulphide bond.

A "stellar" arrangement is indicated in formula III below:

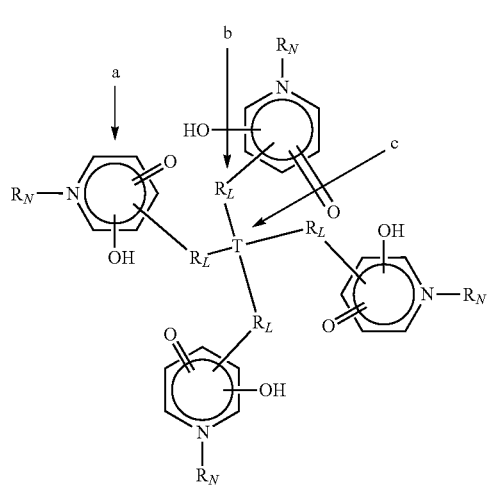

III

An alternative, "backbone" type structure is indicated below in Formula IV

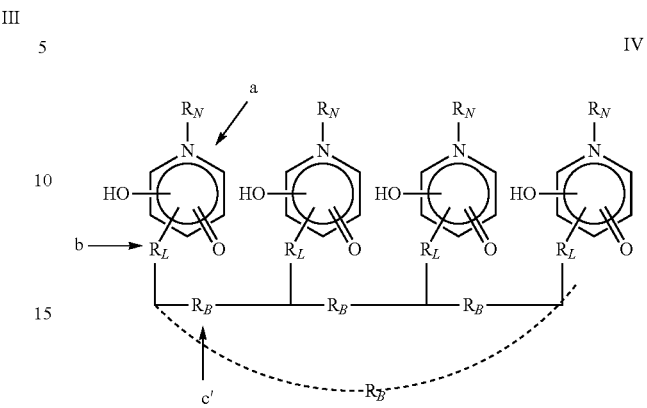

IV

Wherein all groups and positions are as indicated above and "T" is additionally a central atom or template group, such as a carbon atom, hydrocarby chain (such as any of those described herein above), aliphatic or aromatic ring (including heterocyclic rings) or fused ring system. The most basic template would be a single carbon, which would then attach to each of the chelating moieties by their linking groups. Longer chains, such as ethyl or propyl are equally viable with two chelating moieties attaching to each end of the template. Evidently, any suitably robust linkage may be used in joining the template and linker moieties including carbon-carbon bonds, ester, ether, amine, amide, thio-ether or disulphide bonds.

Evidently, in the structures of formula II III, IV and IVb, those positions of the pyridine ring(s) which are not otherwise substituted (e.g by a linker or coupling moiety) may carry substituents described for $R_1$ to $R_5$ in Formula I, as appropriate. In particular, small alkyl substituents, such as methyl, ethyl or propyl groups may be present at any position.

The octadentate ligand will generally additionally comprise at least one coupling moiety as described above. This may be any suitable structure including any of those indicated herein and will terminate with the targeting moiety, a specific binder or a functional group capable of linking to such a targeting moiety or specific binder.

The coupling moiety may attach to any suitable point of the linker, template or chelating moiety, such as at points a), b) and/or c) as indicated in formula III. The attachment of the coupling moiety may be by any suitably robust linkage such as carbon-carbon bonds, ester, ether, amine, amide, thio-ether or disulphide bonds. Similarly, groups capable of forming any such linkages to the targeting moiety are suitable for the functional end of the coupling moiety and that moiety will terminate with such groups when attached to the targeting part.

Wherein all groups and positions are as indicated above and "$R_B$" is additionally a backbone moiety, which will typically be of similar structure and function to any of the linker moieties indicated herein, and thus any definition of a linker moiety may be taken to apply to the backbone moiety where context allow. Suitable backbone moieties will form a scaffold upon which the chelating moieties are attached by means of their linker groups. Usually three or four backbone moieties are required. Typically this will be three for a linear backbone or four if the backbone is cyclised. Particularly preferred backbone moieties include short hydrocarbon chains (such as those described herein) optionally having a heteroatom or functional moiety at one or both ends. Amine and amide groups are particularly suitable in this respect.

The coupling moiety may attach to any suitable point of the linker, backbone or chelating moiety, such as at points a), b) and/or c') as indicated in formula IV. The attachment of the coupling moiety may be by any suitably robust linkage such as carbon-carbon bonds, ester, ether, amine, amide, thio-ether or disulphide bonds. Similarly, groups capable of forming any such linkages to the targeting moiety are suitable for the functional end of the coupling moiety and that moiety will terminate with such groups when attached to the targeting part.

An example of a "backbone" type octadentate ligand having four 3,2-HOPO chelating moieties (each with a hydroxyethyl solubilising group) attached to a backbone by amide linker groups would be formula V as follows:

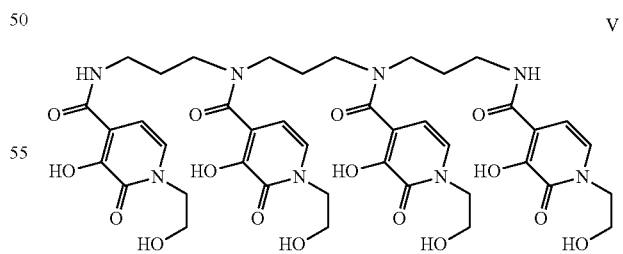

V

Evidently, a linker group $R_L$ may be added at any suitable point on this molecule, such as at one of the secondary amine groups or as a branching point on any of the backbone alkyl groups. All small alkyl groups such as the backbone propylene or the n-substituting ethylene groups may be substituted with other small alkylenes such as any of those described herein (methylene, ethylene, propylene, and butylene being highly suitable among those).

Exemplary "templated" octadentate ligands, each having four 3,2-HOPO chelating moieties linked by ethyl amide groups to ethyl and propyl diamine respectively would be formula VI as follows:

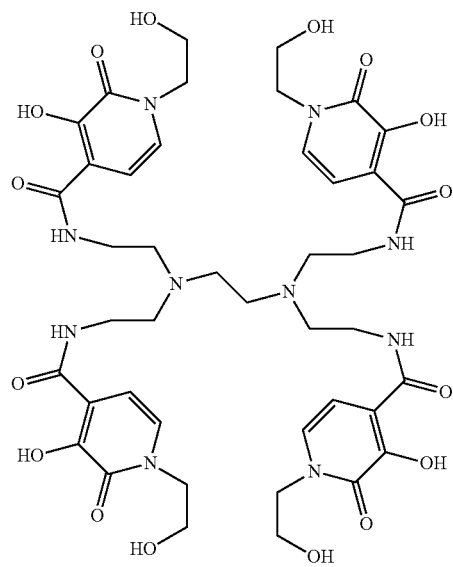

VI

Evidently, any of the alkylene groups, shown in formula VI as ethylene moieties may be independently substituted with other small alkylene groups such as methylene, propylene or n-butylene. It is preferred that some symmetry be retained in the molecule and thus, for example, the central ethylene group might be substituted with a propylene while the other ethylene groups remain, or the two ethylenes linking the HOPO moieties to one or both central tertiary amines may be replaced with methylene or propylene. Similarly, as discussed herein, the N-substituting groups may be replaced with any other hydroxyalkyl group as discussed herein throughout.

As indicated above, the octadentate ligand will typically include a coupling moiety which may join to the remainder of the ligand at any point. A suitable point for linker attachment is shown below in formula VI:

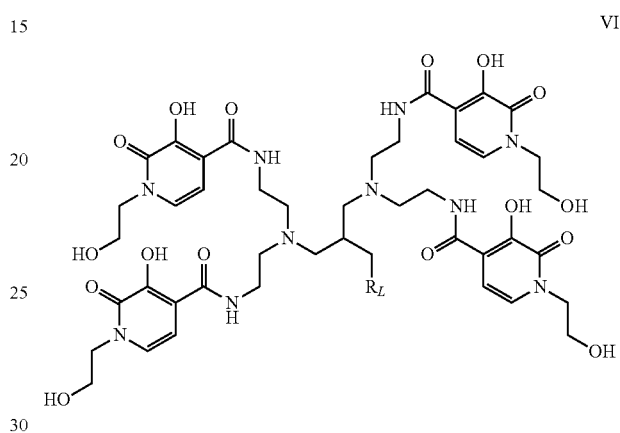

VI

Wherein $R_L$ is any suitable linking moiety, particularly for attachment to a tissue targeting group. A short hydrocarbyl group such as a C1 to C8 cyclic, branched or straight chain aromatic or aliphatic group terminating in an active group such as an amine is highly suitable as group $R_L$ in formula VI and herein throughout.

Highly preferred octadentate ligands showing suitable sites for ligand attachment include those of formulae VII and VIII below:

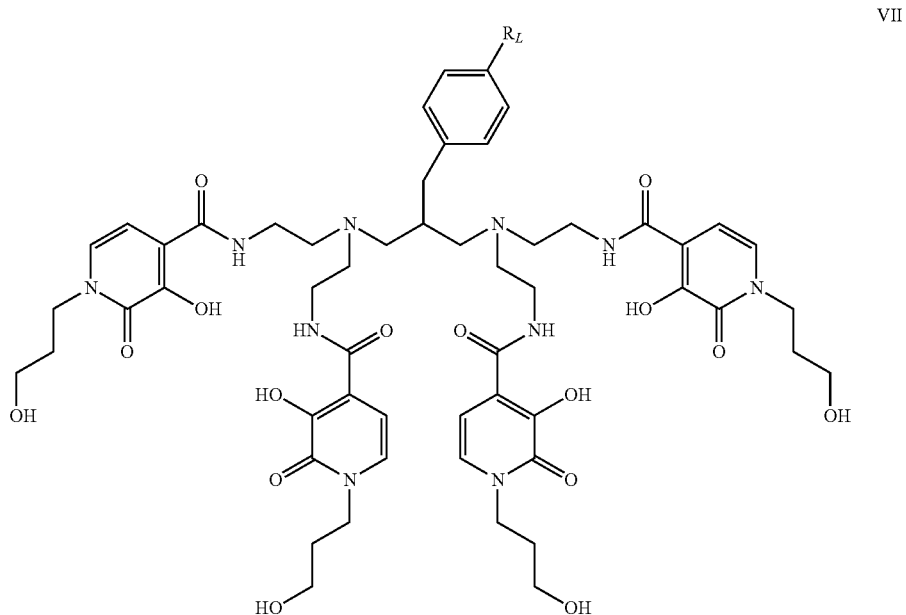

VII

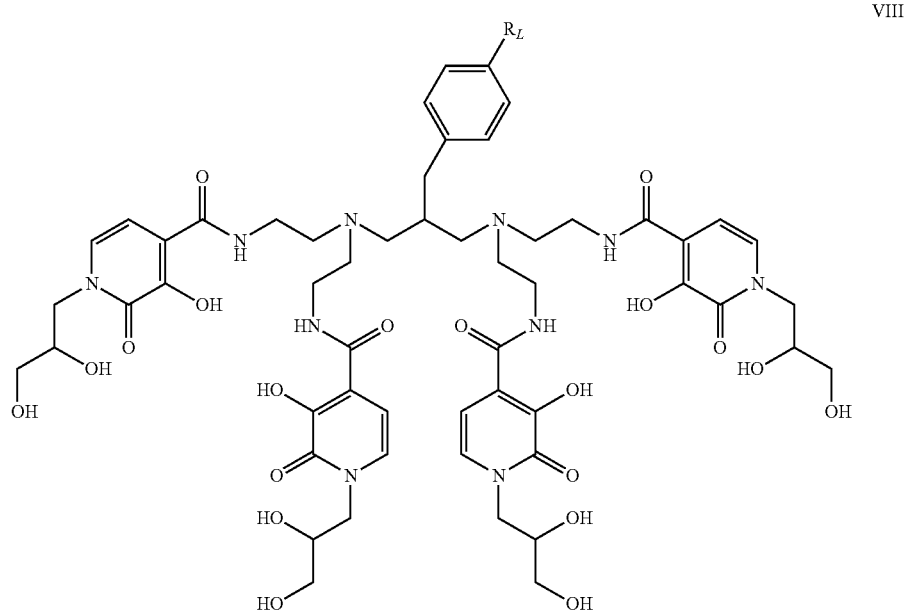

Wherein in formulae VII and VIII $R_L$ may be any suitable linker group or reactive moiety as described herein. $R_L$ will typically form the point of attachment of the ligand to the targeting moiety and thus any suitable reactive group can be used for this attachment either directly or using a further linker. Suitable reactive moieties for $R_L$ in formulae VII and VIII include $NH_2$ and NCS groups.

An exemplary compound with a functionalized moiety terminating the coupling moiety, according to this embodiment, is structure IX below (the linker phenylamine group may evidently be substituted with any other $R_L$ group as indicated herein as appropriate):

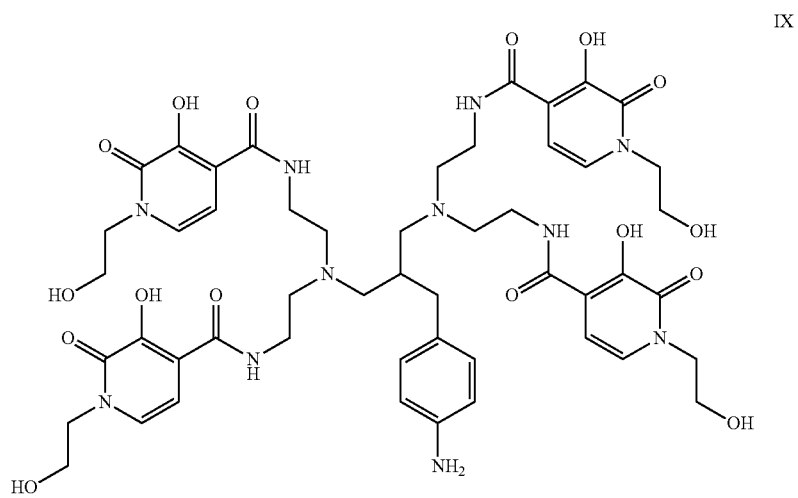 [SMILES: Nc1ccc(CC(CN(CCNC(=O)c2ccn(CCO)c(=O)c2O)CCNC(=O)c2ccn(CCO)c(=O)c2O)CN(CCNC(=O)c2ccn(CCO)c(=O)c2O)CCNC(=O)c2ccn(CCO)c(=O)c2O)cc1]

The synthesis of compound IX is described herein below and follows the following synthetic route:

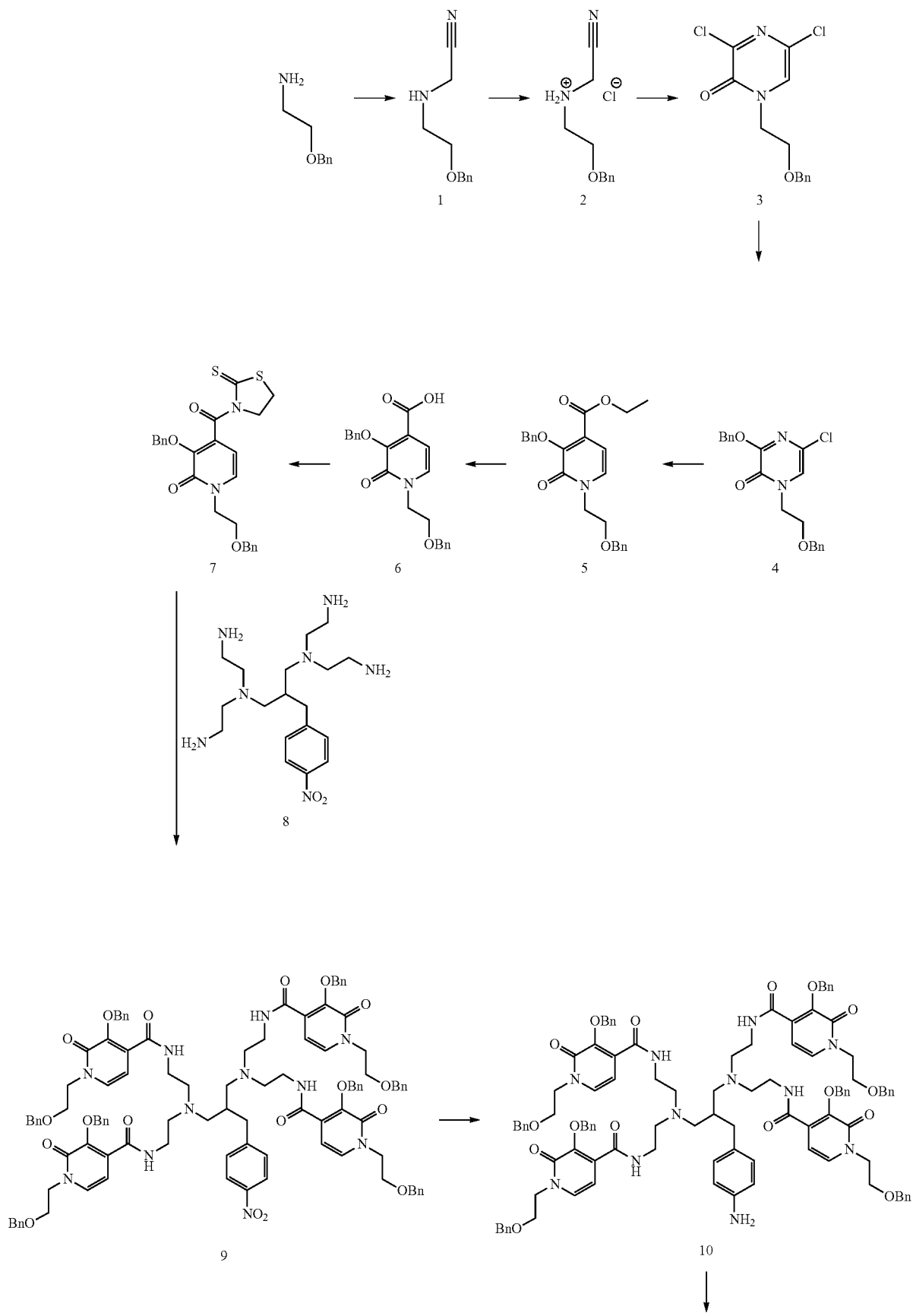

-continued

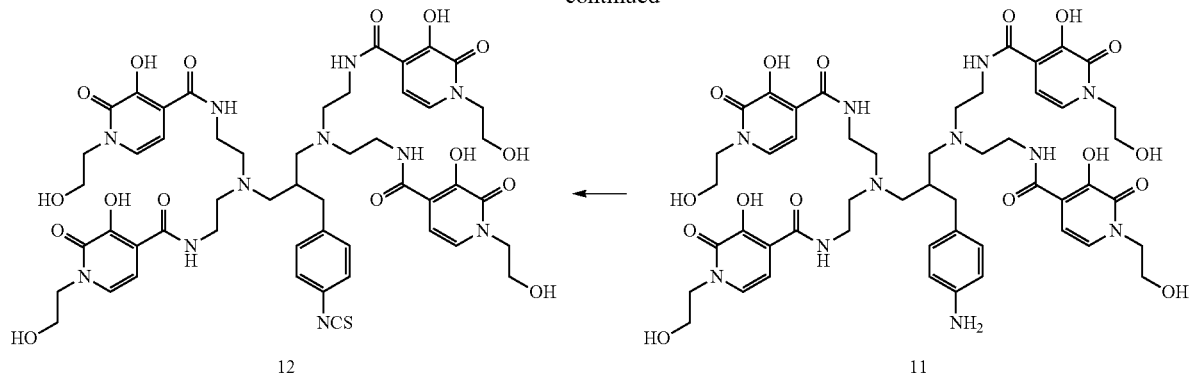

All documents referred to herein are hereby incorporated by reference, including Gordon A E V et al, Rational design of sequestering agents for plutonium and other actinides. Chem. Rev. 2003, 103, 4207-4282, PCT Patent Application WO 2008/063721 A2 and T. N. Lambert et al., Tetrahedron Letters 43 (2002) 7379-7383.

In the methods of formation of the complexes of the present invention, it is preferred that the reaction be carried out in aqueous solution. This has several advantages. Firstly, it removes the burden on the manufacturer to remove all solvent to below acceptable levels and certify that removal. Secondly it reduces waste and most importantly it speeds production by avoiding a separation or removal step. In the context of the present radiopharmaceuticals, it is important that synthesis be carried out as rapidly as possible since the radioisotope will be decaying at all times and time spent in preparation wastes valuable material and introduces contaminant daughter isotopes.

In one embodiment, the method comprises forming a first aqueous solution of octadentate hydroxypyridinone-containing ligand (as described herein throughout) and a second aqueous solution of a tissue targeting moiety (as described herein throughout) and contacting said first and said second aqueous solutions.

In a related embodiment, the method of formation of the present invention is carried out in the substantial absence of any organic solvent. In this context, and "organic solvent" takes its natural meaning of a material which is liquid at or around room temperature and which comprises at least one carbon. Such organic solvents typically comprise hydrocarbon, alcohol, ester, amide, ester and/or halogenated moieties and such solvents are preferably present at no more than 1% (e.g. 0.0001 to 1%), preferably no more than 0.5% and most preferably no more than 0.2% by weight in the aqueous solutions referred to herein. For the avoidance of doubt, the targeting moieties and ligands referred to herein are not encompassed by the term "organic solvent". Certain organic materials, such as organic acids, amines and their salts may be present at somewhat higher concentrations so as to act as pH buffers in the aqueous solvent. Where present these will typically be at a concentration of no more than 10% (e.g. 0.001 to 10%), preferably no more than 5%, more preferably no more than 1% by weight. Generally these compounds are not liquid at room or ambient temperature and thus are not organic solvents.

Suitable coupling moieties are discussed in detail above and all groups and moieties discussed herein as coupling and/or linking groups may appropriately be used for coupling the targeting moiety to the ligand. Some preferred coupling groups include amide, ester, ether and amine coupling groups. Esters and amides may conveniently be formed by means of generation of an activated ester groups from a carboxylic acid. Such a carboxylic acid may be present on the targeting moiety, on the coupling moiety and/or on the ligand moiety and will typically react with an alcohol or amine to form an ester or amide. Such methods are very well known in the art and may utilise well known activating reagents including N-hydroxy maleimide, carbodiimide and/or azodicarboxylate activating reagents such as DCC DIC DEAD DIAD etc.

BRIEF SUMMARY OF THE FIGURES

FIGS. 4A and B: HL-60 lymphoma cells incubated with the Th-227 labelled AGC0015 conjugated CD33-binding mAb AGC0715 (filled circles), the Th-227 labelled AGC0015 conjugated control mAb trastuzumab (filled squares), or culture medium (filled diamonds). Both mAbs were labelled with Th-227 to the same specific activity, and used at either 3 nM (A) or 0.3 nM (B).

was plotted against log concentration in nM of primary antibody. Trastuzumab was used as an isotype control.

Figures 7, 8:
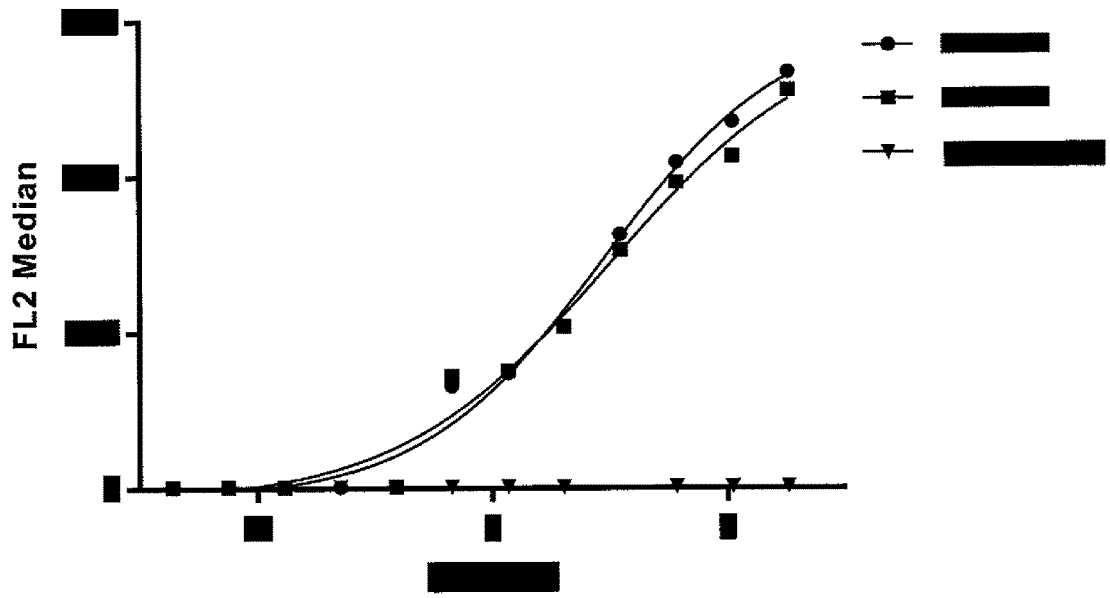
FIG. 7 Binding of AGC1100 and AGC1115 analysed by flow cytometry on CD22-positive Raji cells. Detection was done using mouse anti-human IgG Fc, PE conjugated secondary antibody and median fluorescence intensity (MFI)

FIG. 8: Ramos cells incubated with the Th-227 labelled AGC0015 conjugated C22-binding mAb AGC1115 (filled circles), the Th-227 labelled AGC0015 conjugated control mAb trastuzumab (filled squares), or culture medium (filled diamonds). Both mAbs were labelled with Th-227 to the same specific activity (44 kBq/µg), and used at 3 nM (A).

FIG. 9: HPLC Analysis of product 15 of Example 18. Starting material 11 is shown at 6.041 minutes, desired amide product 15 at 7.616 minutes and diacylated side-product at 8.157 minutes.

FIG. 10: FPLC-SEC, chromatogram of AGC0203, (FIG. 10A), and AGC0215, (FIG. 10B). Absorbance monitored at 280 nm. The total area under peaks was determined to 166 mAU*mL and 409 mAU*mL, respectively.

Figure 11:
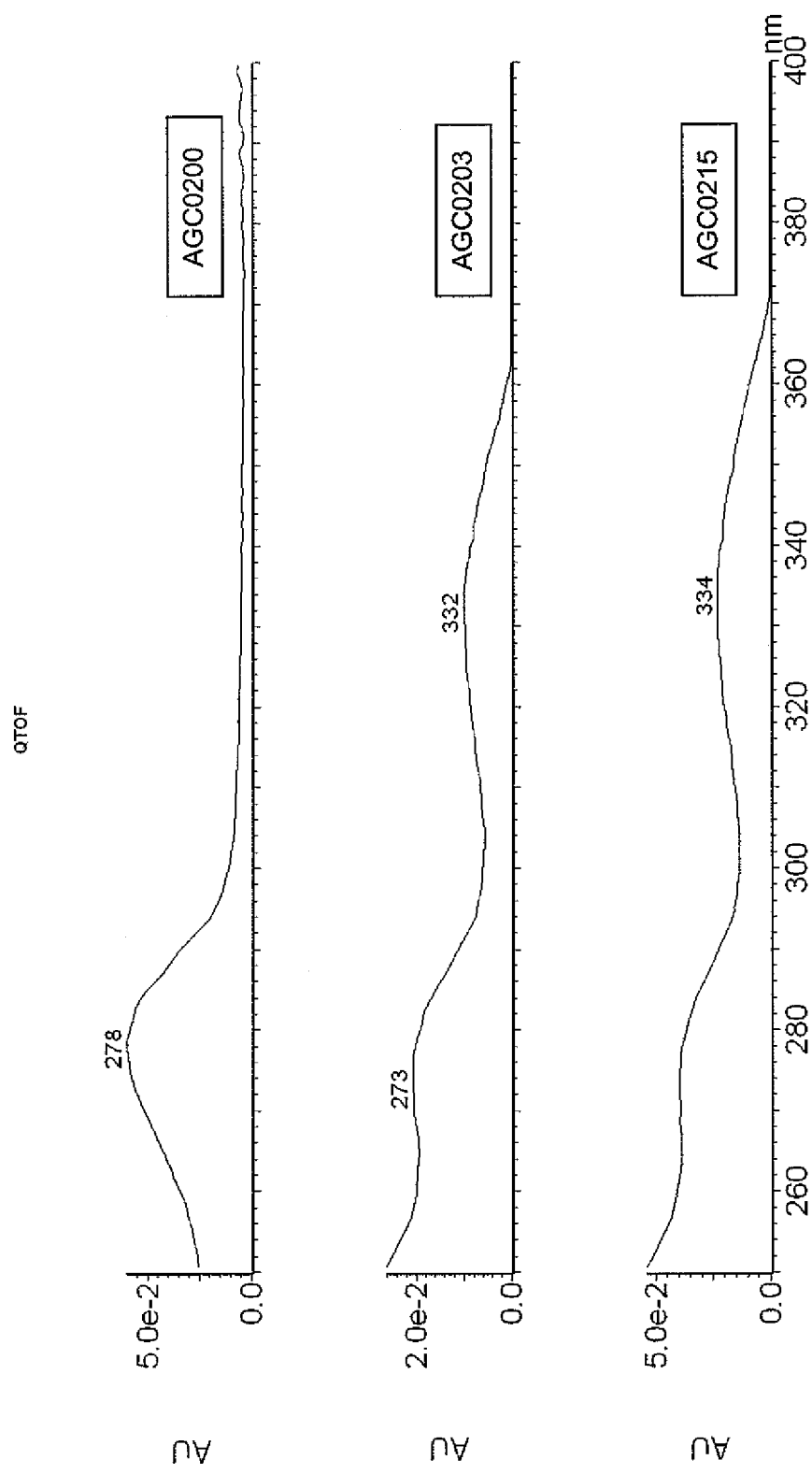

FIG. 11: Diode array spectrophotometric analysis of the main protein fraction of AGC0200, AGC0203 and AGC0215 separated by size exclusion chromatography. The chelator in the conjugate absorbs at approximately 335 nm, the protein at around 280 nm.

Figure 12A:
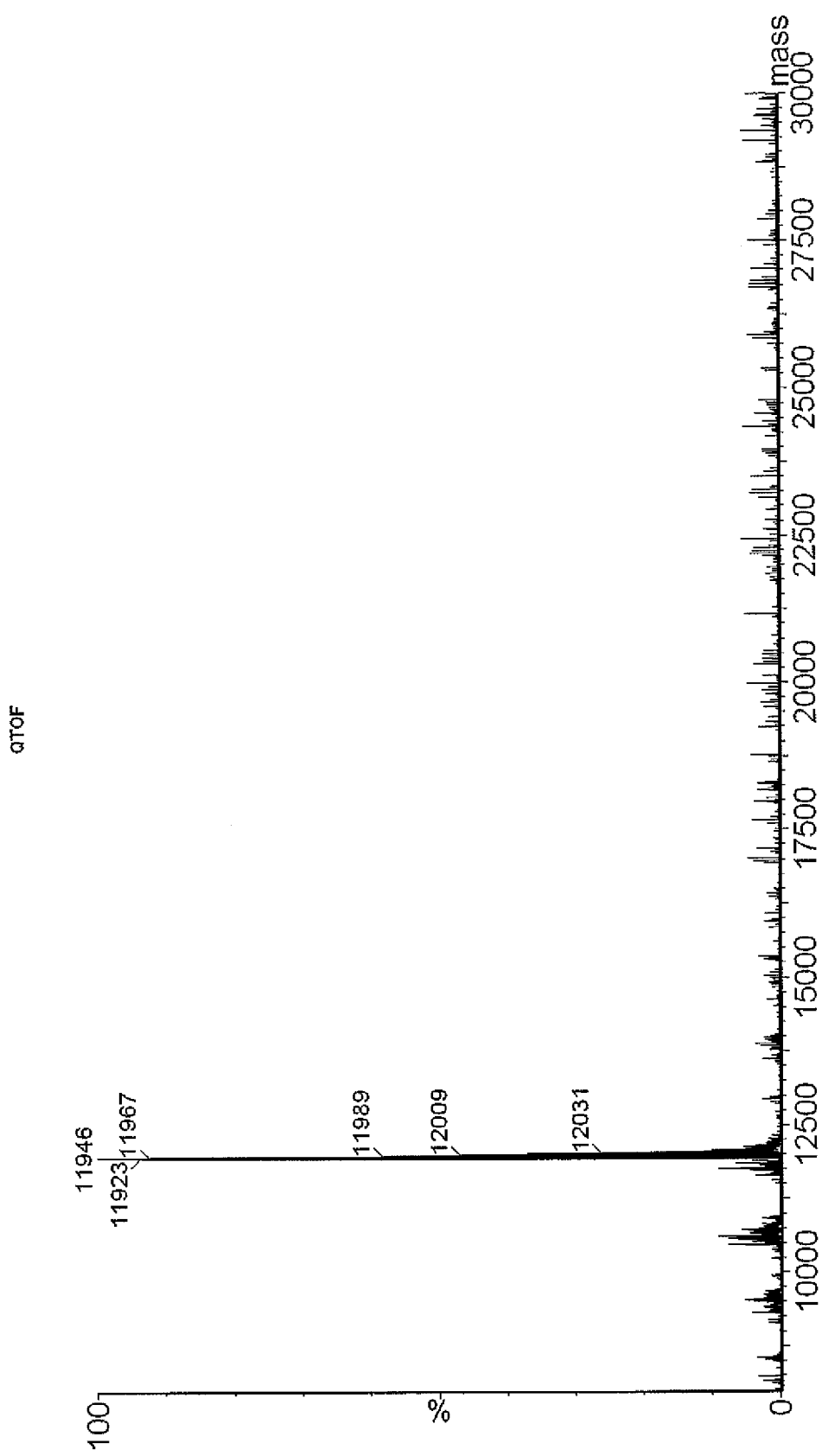
Figure 12B:
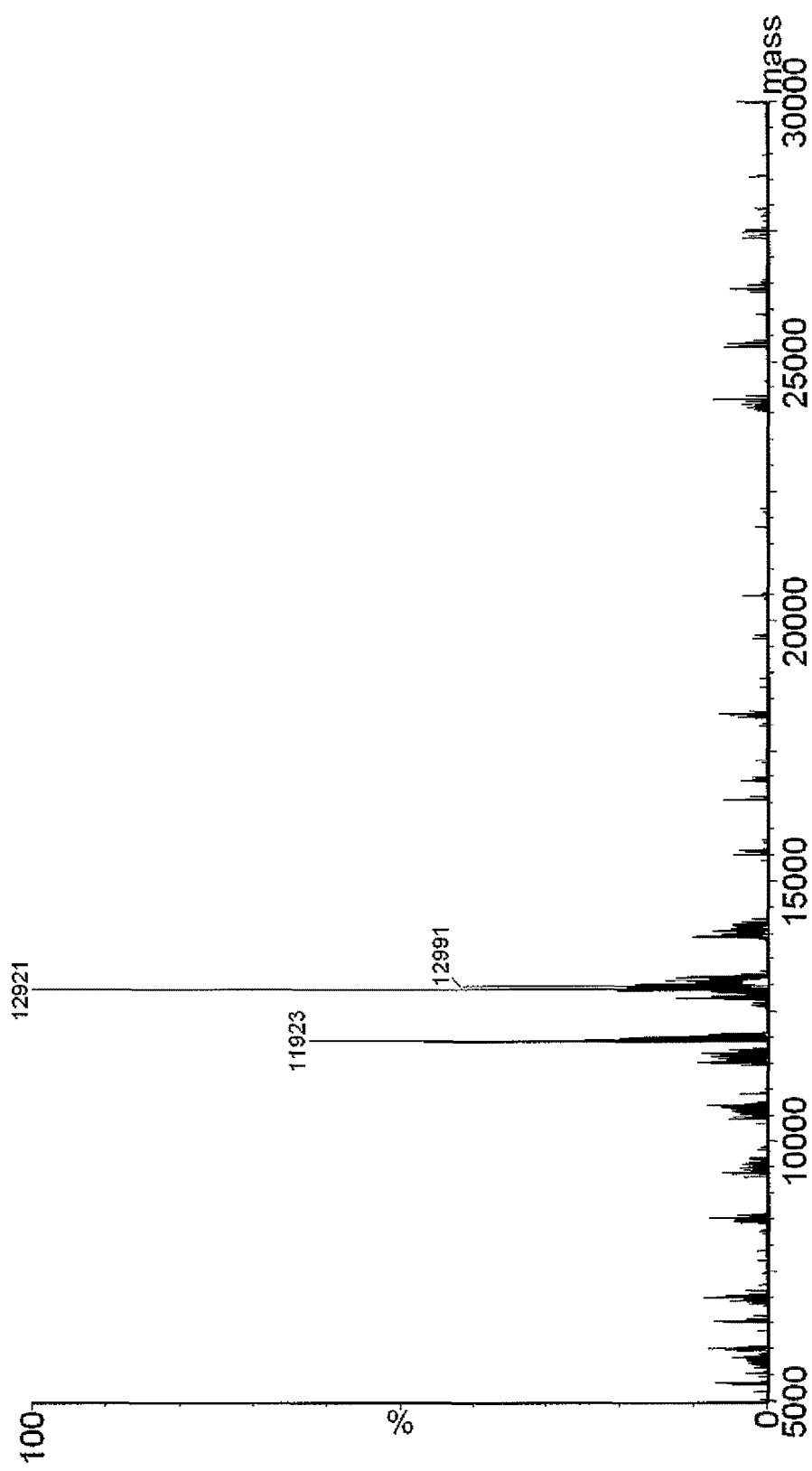
Figure 12C:
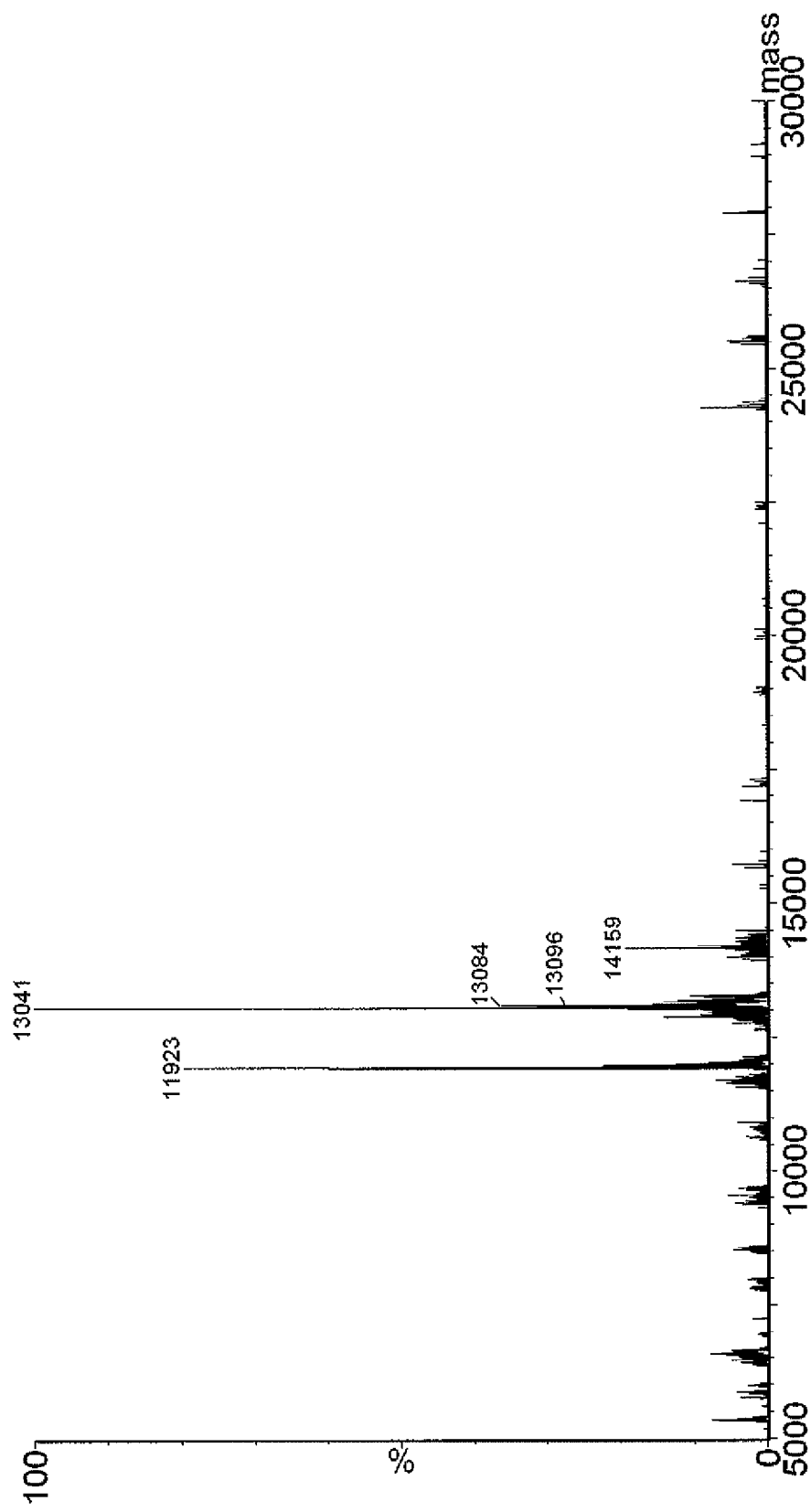

FIG. 12: MS spectra of the preparations of AGC0200 (12A), AGC0203 (12B), and AGC0215 (12C).

The invention will now be illustrated by the following non-limiting Examples. All compounds exemplified in the examples form preferred embodiments of the invention (including preferred intermediates and precursors) and may be used individually or in any combination in any aspect where context allows. Thus, for example, each and all of compounds 2 to 4 of Example 2, compound 10 of Example 3 and compound 7 of Example 4 form preferred embodiments of their various types.

In the Examples, the following ligands, antibodies and antibody conjugates are referred to:

AG0003—Comparative ligand (structure 13 below)
AG0015—High solubility ligand of the invention.
AG0700—Anti-CD33 antibody as generated in Example 5
AG0715—AG0700 conjugated to a high-solubility ligand (12)
AGC1100—Anti-DC22 antibody as generated in Example (13)
AGC1115—AGC1100 conjugated to a high-solubility ligand (12)

EXAMPLE 1

Isolation of Pure Thorium-227

Thorium-227 is isolated from an actinium-227 cow. Actinium-227 was produced through thermal neutron irradiation of Radium-226 followed by the decay of Radium-227 (t½=42.2 m) to Actinium-227. Thorium-227 was selectively retained from an Actinium-227 decay mixture in 8 M $HNO_3$ solution by anion exchange chromatography. A column of 2 mm internal diameter, length 30 mm, containing 70 mg of AG®1-X8 resin (200-400 mesh, nitrate form) was used. After Actinium-227, Radium-223 and daughters had eluted from the column, Thorium-227 was extracted from the column with 12 M HCl. The eluate containing Thorium-227 was evaporated to dryness and the residue resuspended in 0.01 M HCl.

EXAMPLE 2

Synthesis of Compound IX

Step 1

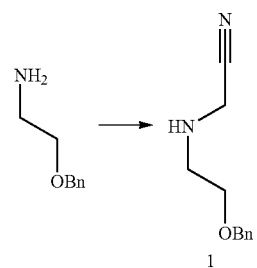 [SMILES: NCCOCc1ccccc1 ; N#CCNCCOCc1ccccc1]

2-benzyloxyethylamine (31 g, 207 mmol) and glycolonitrile (16 mL, 70% solution in water, 207 mmol) was dissolved in 300 mL EtOH (abs) and refluxed for 4 h. The volatiles were removed under reduced pressure. The crude product (24.7 g, 130 mmol) was carried on to the next step without further purification.

$^1$H-NMR (CDCl$_3$, 400 MHz): 2.92 (m, 2H), 3.58-3.62 (m, 4H), 4.51 (s, 2H), 7.25-7.37 (m, 5H)

Step 2

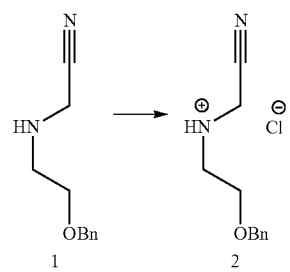 [SMILES: N#CCNCCOCc1ccccc1 ; N#CC[NH2+]CCOCc1ccccc1 ; [Cl-]]

1 (24.7 g, 130 mmol) was dissolved in dry ether. HCl (g) was bubbled through the solution for 30 minutes. The precipitate was filtered off and dried under reduced pressure, giving the desired product (27.8 g, 122.6 mmol. The product was carried on to the next step without further purification or analysis.

Step 3

2 (27.8 g, 122.6 mmol) was dissolved in 230 mL chlorobenzene at room temperature. Oxallyl chloride (45 mL, 530 mmol) dissolved in 100 mL chlorobenzene was added drop wise over 30 minutes at room temperature. The reaction mixture was stirred at room temperature for 45 hours.

The reaction was carefully quenched by drop wise addition of 100 mL water. The phases were separated, and the aqueous phase was extracted with 3*100 mL DCM. The organic phases were combined and washed with 100 mL brine. The organic phase was dried over Na$_2$SO$_4$, filtered and the volatiles were removed under reduced pressure. The crude product was purified by dry flash chromatography on SiO$_2$ using a gradient of MeOH (0-2%) in DCM, yielding the desired product (21.2 g, 70.8 mmol).

$^1$H-NMR (CDCl$_3$, 400 MHz): 3.71-3.76 (m, 2H), 4.06-4.12 (m, 2H), 4.47 (s, 2H), 7.217-7.22 (m, 2H), 7.26-7.36 (m, 4H)

MS(ESI-pos, m/z,): 321.0

Step 4

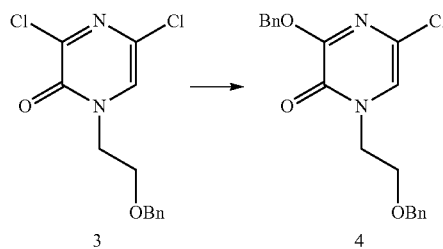

Sodium hydride (60% dispersion, 3.60 g, 90 mmol) was stirred in 50 mL THF at 0° C. and benzyl alcohol (8.3 mL, 80 mmol) was added drop wise over 10 minutes. The reaction mixture was stirred for 30 minutes at 0° C. before 3 (21.2 g, 70.8 mmol) dissolved in 100 mL THF was added drop wise at 0° C. The reaction mixture was stirred in the dark over night at room temperature. 50 mL HCl in dioxane (4M) was added drop wise before the reaction mixture was reduced in vacuo. 500 mL DCM was added, followed by 200 mL water. The phases were separated and the aqueous phase was extracted with 200 mL DCM. The organic phases were combined and washed with 100 mL brine. The organic phase was dried over Na$_2$SO$_4$, filtered and the volatiles were removed under reduced pressure. Dry flash chromatography on SiO$_2$ using a gradient of MeOH (0-6%) in DCM gave the desired product (25.6 g, 69 mmol).

$^1$H-NMR (CDCl$_3$, 300 MHz): 3.69-3.75 (m, 2H), 4.01-4.07 (m, 2H), 4.46 (s, 2H), 5.37 (s, 2H), 6.97 (s, 1H), 7.19-7.39 (m, 8H), 7.44-7.51 (m, 2H)

MS(ESI-pos, m/z): 371.1, 763.2

Step 5

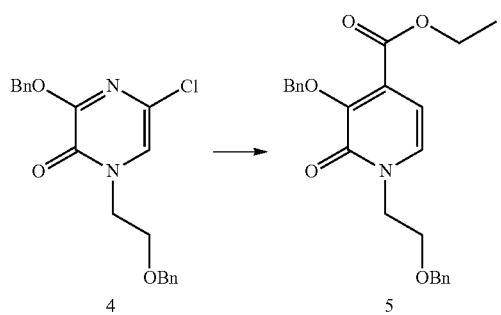 [SMILES: O=c1c(OCc2ccccc2)nc(Cl)cn1CCOCc1ccccc1 ; CCOC(=O)c1ccn(CCOCc2ccccc2)c(=O)c1OCc1ccccc1]

4 (25.6 g, 69 mmol) and ethyl propiolate (41 mL, 0.4 mol) was heated at 140° C. for 5 hours. The reaction mixture was cooled down to room temperature and the reaction mixture was purified by dry flash chromatography on SiO$_2$. A gradient of MeOH (0-10%) in DCM gave the desired product as an inseparable mixture of the desired 4-isomer together with the 5-isomer. This mixture (28.6 g, ~65 mmol) was used directly in the next step without further purification.

Step 6

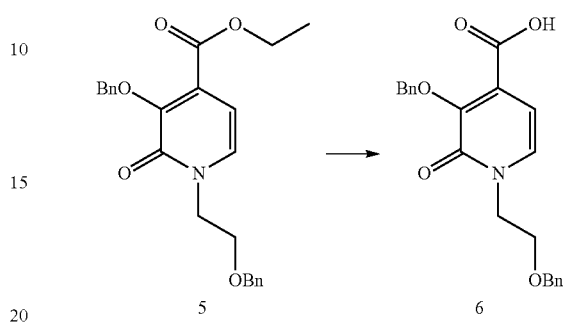

5 (28.6 g, ~65 mmol), as obtained in the previous step, was dissolved in 300 mL THF at 0° C. 100 mL KOH (1M, aq) was added, and the reaction mixture was stirred for 40 hours at room temperature. HCL (1M, aq) was added until pH~2 (125 mL) and the aqueous phase was extracted with 3*250 mL CHCl$_3$. The organic phases were combined and washed with 100 mL brine, filtered and the volatiles were removed in vacuo. The obtained material (25.9 g, ~65 mmol) was used without in the next step without further purification or analysis.

Step 7

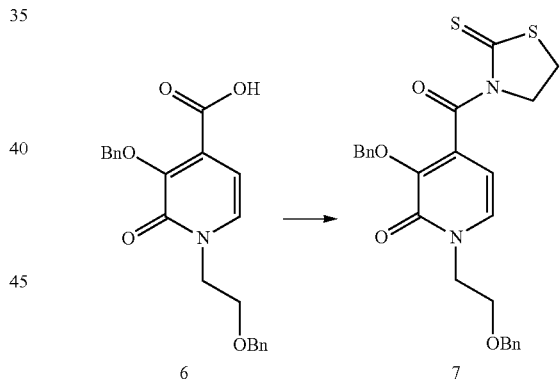

6 (25.9 g, ~64 mmol), as obtained in the previous step, was partially dissolved in 400 mL DCM. 2-Thiazoline-2-thiol (8.94 g, 75 mmol) and DMAP (0.86 g, 7 mmol) was added, followed by DCC (15.48 g, 75 mmol). The reaction mixture was stirred at room temperature over night. The reaction mixture was filtered through a Celite-pad and the Celite-pad was washed with 100 mL DCM. The volatiles were removed in vacuo. The product mixture was purified by dry flash chromatography on SiO$_2$ using first a gradient of DCM (50-100%) in heptane, followed by a gradient of THF (0-15%) in DCM. The appropriate fractions were reduced in vacuo, giving a mixture of products. This inpure mixture was purified by flash chromatography on SiO$_2$ using a gradient of EtOAc (25-75%) in heptane. The appropriate fractions were reduced in vacuo, giving a mixture of products. Finally, to get the desired product, the product mixture was purified by dry flash chromatography on RP18-silica using a gradient of MeCN (25-75%) in water. This gave the desired product (8.65 g, 18 mmol).

¹H-NMR (CDCl₃, 300 MHz): 2.90 (t, J=7.3 Hz, 2H), 3.77-3.84 (m, 2H), 4.18-4.23 (m, 2H), 4.35 (t, J=7.3 Hz, 2H), 4.51 (s, 2H), 5.33 (s, 2H), 6.11 (d, 7.0 Hz, 1H), 7.21-7.48 (m, 11H)

MS(ESI-pos, m/z): 503.1

Step 8

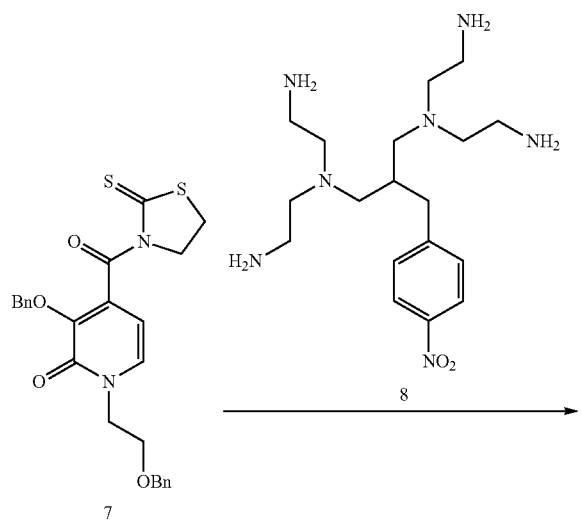

7

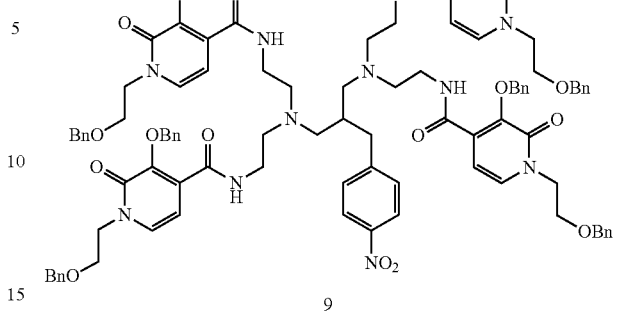

9

7 (5.77 g, 12 mmol) and 8 (1.44 g, 2.4 mmol) were partially dissolved in 40 mL DMPU. DBU (2.7 mL, 18 mmol) was added drop wise. The reaction was stirred for 4 days at room temperature. Purification by dry flash chromatography on SiO₂ using a gradient of DCM and MeOH in EtOAc gave the desired product (3.93 g, 2.15 mmol).

¹H-NMR (CDCl₃, 400 MHz): 2.20-2.32 (m, 10H), 2.44-2.50 (m, 2H), 3.05-3.20 (m, 10H), 3.23-3.27 (m, 1H), 3.69-3.77 (m, 8H), 4.06-4.15 (m, 8H), 4.43 (s, 8H), 5.24 (s, 8H), 6.62 (d, J=7.2 Hz, 4H), 7.13 (d, J=7.2 Hz, 4H), 7.16-7.38 (m, 42H), 7.82-7.93 (m, 6H)

Step 9

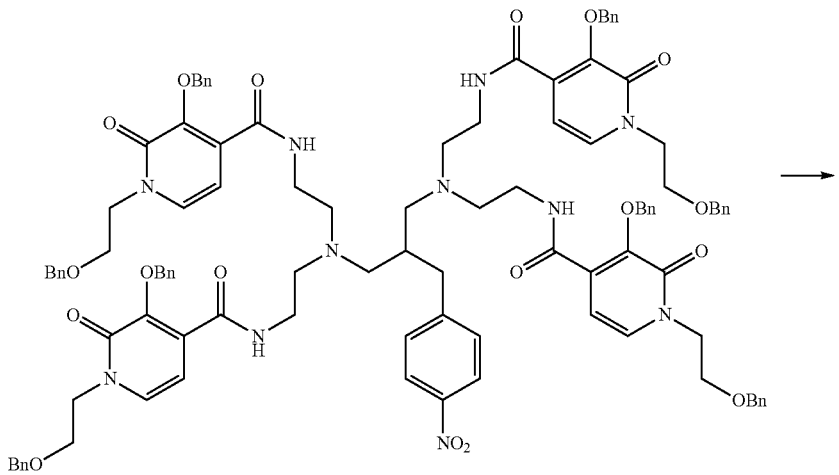

9

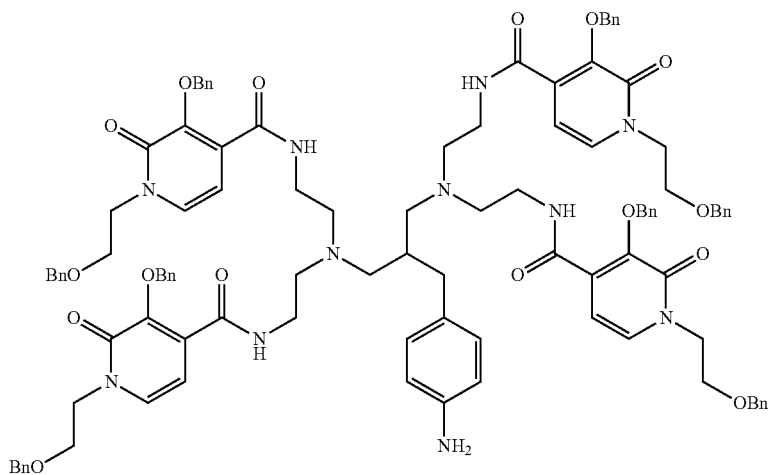

10

9 (3.93 g, 2.15 mmol) was dissolved in 300 mL EtOH at room temperature. 60 mL water was added, followed by NH$_4$Cl (5.94 g, 32.3 mmol). The reaction mixture was to 60° C. before iron powder (1.80 g, 32.3 mmol) was added. The reaction mixture was stirred at 60° C. for 1 hour. The reaction mixture was cooled down to room temperature and 400 mL DCM and 100 mL water was added. The reaction mixture was filtered, and the organic phase was washed with 100 mL water and 100 mL brine. The aqueous phases were combined and back extracted with 3*100 mL DCM. The organic phases were combined, dried over Na$_2$SO$_4$, filtered and the volatiles were removed under reduced pressure. The product mixture was purified by dry flash chromatography on SiO2 using a gradient of MeOH (0-7%) in DCM gave the desired product (3.52 g, 1.96 mmol).

MS(ESI-pos, m/z): 899.2

Step 10

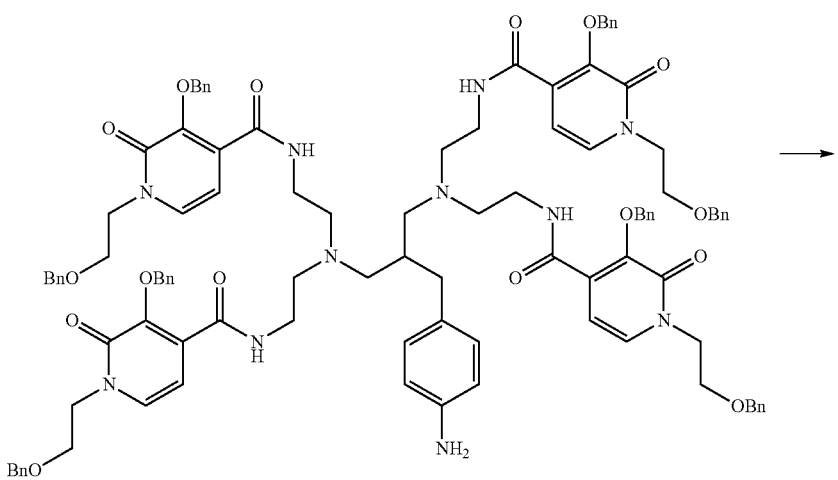

10

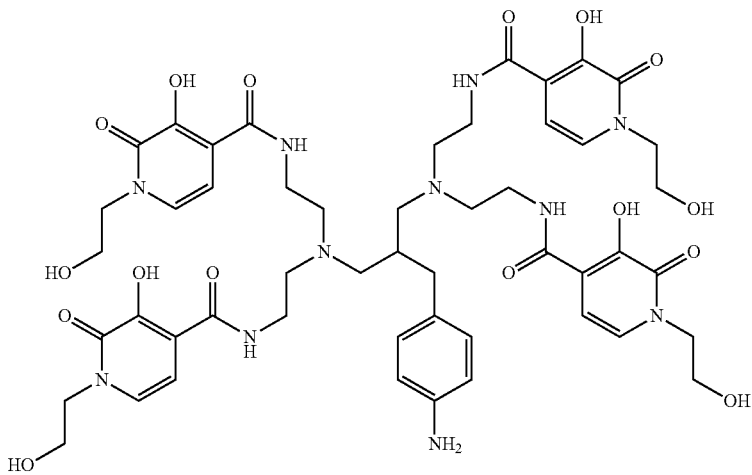

11

10 (1.00 g, 0.56 mmol), Pd(OH)$_2$/C (Pearlman's catalyst, 1.00 g) and 10 mL AcOH was placed in a pressure reactor. The reactor was evacuated by water aspirator and H$_2$ was introduced (7 bar). The reaction mixture was stirred for 1 hour before the pressure was released and 5 mL HCl (6M, aq) was added to the reaction mixture. The reactor was evacuated as before and H$_2$ was once again introduced (7 bar). After stirring for 7 days, HPLC indicated full conversion. The reaction mixture was filtered and the volatiles were removed under reduced pressure. The residue was dissolved in MeOH/MeCN (1:1) and the product was precipitated by addition of Et$_2$O. The solids were collected by centrifugation and decanting the supernatant before the product was dried in vacuo (484 mg, 0.45 mmol).

$^1$H-NMR (D$_2$O, 400 MHz): 2.70-2.95 (m, 2H), 3.00-3.10 (m, 2H), 3.15-3.65 (m, 19H), 3.75-4.23 (m, 16H), 6.25 (bs, 4H), 7.04 (d, J=7.0 Hz, 4H), 7.44 (d, J=8.2 Hz, 2H), 7.57 (d, J=8.2 Hz, 2H)

MS(ESI-pos, m/z): 1076.4

Step 11

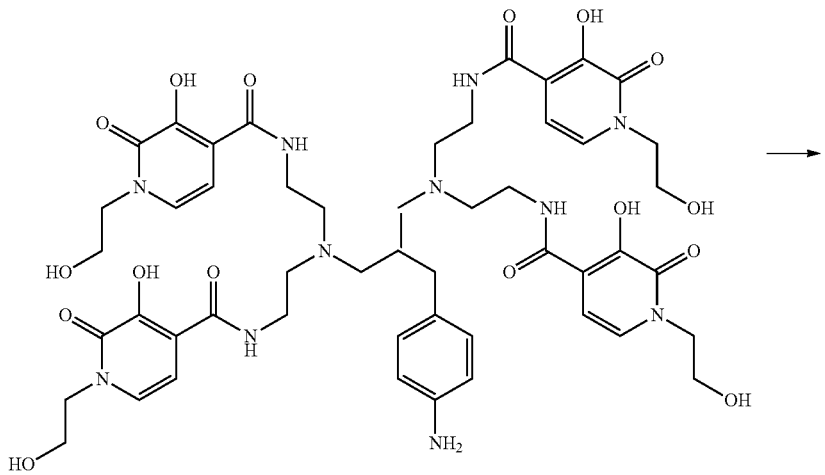

11

-continued

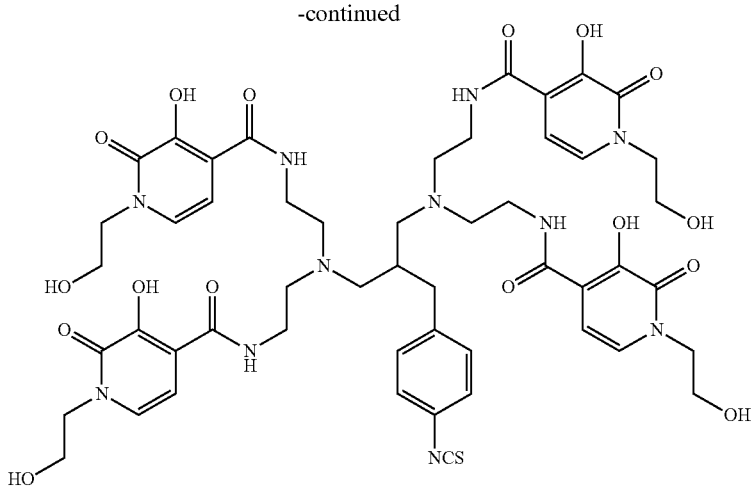

12

Compound 11 (20 mg, 18 μmol) was dissolved in 3 mL MeCN and 3 mL water. 20 μL thiophosgene was added. The reaction mixture was stirred rigidly for 1 hour. The volatiles were removed under reduced pressure and the residue was dissolved in 4 mL MeCN. The product was precipitated by adding the acetontrile phase to 40 mL Et$_2$O. The solids were collected by centrifugation and decating the supernatant before the product was dried in vacuo (10 mg, 9 μmol).

MS(ESI-pos, m/z): 1118.4

EXAMPLE 3

Conjugation

Filtered trastuzumab in 1.0 mL 0.9% NaCl solution (9.5 mg/mL), and novel chelator (formula IX) in 5-35 μL metal free water (10 mg/mL) were added to 1.0 mL sterile filtered borax buffer (70 mM, pH 9). The reaction mixture was stirred gently at 37° C. over night, and the resulting conjugate was purified and concentrated in 0.9% NaCl solution using an Amicon Ultra-4 (30 k MWCO) centrifugal filter unit. Successful conjugation was confirmed by LC/MS analysis.

EXAMPLE 4

Chelation

The conjugate of Example 3 in 50 μL 0.9% NaCl (5 μg/μL) was added 100 μL sodium acetate buffer (0.5 M, pH 5.5), and then $^{227}$Th-solution (approx. 0.5-1 MBq in 1-4 μL 0.05 M HCl). Reaction was done under gentle mixing at 37° C. for 1 hour or at room temperature (approx. 20° C.) for 15 minutes, and the resulting product purified on NAP-5 column using sodium acetate buffer as eluting buffer. The spent column containing retained free radiometals and the eluted fractions containing labelled protein were measured on a HPGe-detector GEM (15), to determine reaction yields and specific activity of the product (Table 1).

TABLE 1

| Summary, chelation reactions | |
|---|---|
| Reaction conditions | Radiochemical yield (%) |
| 37° C., 1h | 96 |
| 37° C., 1h | 93 |
| 20° C., 15 min | 95 |
| 20° C., 15 min | 95 |

EXAMPLE 5

Generation of the Anti-CD33 Monoclonal Antibody (AGC0700)

The sequence of the monoclonal antibody (mAb) HuM195 as described in (1) and published in (2) served as template for the generation of AGC0700. The codon encoding the C-terminal lysine (Lys) was omitted from the IgG1 heavy chain gene. The resulting protein is one of three variants that are present in the antibody when produced from the full length genes, the other two variants having a lysine attached at one or both of the heavy chains, respectively. It is anticipated that removal of this Lys-residue allows a more precise determination of the conjugate to antibody ratio (CAR) as outlined in Example 6. An overview of the complete amino acid sequence of AGC0700 is presented in Table 2.

The genes encoding AGC0700 were generated using standard molecular biology techniques. Briefly, the amino acid sequence of each chain was back-translated into DNA sequence using Vector NTI® Software (Invitrogen/Life-Technologies Ltd., Paisley, United Kingdom). The optimized DNA sequence was codon optimized for mammalian expression and synthesized by GeneArt (GeneArt/Life-Technologies Ltd., Paisley, United Kingdom). The VH- and VL-domains were sub-cloned via endonuclease restriction digest into an expression vector by Cobra Biologics (Sodertalje, Sweden). Chinese hamster ovarian suspension (CHO-S) cells were stably transfected with the plasmid encoding the VH- and VL-domains of AGC0700 and grown in presence of standard CD-CHO medium (Invitrogen/Life-Technologies Ltd., Paisley, United Kingdom), supplemented with puromycin (12.5 mg/l; Sigma Aldrich). Stable clones, expressing AGC0700, were selected via limiting dilution over 25 generations. Clone stability was assessed by measuring protein titers from supernatants. A cell bank of the most stable clone was established and cryo-preserved. Expression of the mAb was carried out at 37° C. for approximately 14 days in a single-use bioreactor. The monoclonal antibody was harvested after filtration of the supernatant. AGC0700 is further purified by protein A affinity chromatography (MabSelect SuRe, Atoll, Weingarten/Germany), followed by an ion exchange step. A third purification step based on electrostatic and hydrophobicity is used to further remove aggregates and impurities from production. The identity of AGC0700 will be confirmed by isoelectric focusing and SDS-PAGE analysis. Sample purity will be further analyzed by size-exclusion chromatography (SEC).

TABLE 2

Amino acid sequence of AGC0700.

| | |
|---|---|
| Fragment variable $V_H$ domain (SeqID 1) | QVQLVQSGAEVKKPGSSVKVSCKASGYTFTDYNMHWVRQAPGQGLEWIGYIYPYNG GTGYNQKFKSKATITADESTNTAYMELSSLRSEDTAVYYCARGRPAMDYWGQGTLV TVSS |
| Fragment variable $V_L$ domain (SeqID 2) | DIQMTQSPSSLSASVGDRVTITCRASESVDNYGISFMNWFQQKPGKAPKLLIYAAS NQGSGVPSRFSGSGSGTDFTLTISSLQPDDFATYYCQQSKEVPWTFGQGTKVEIK |
| Complete $V_H$ domain (SeqID 3) | QVQLVQSGAEVKKPGSSVKVSCKASGYTFTDYNMHWVRQAPGQGLEWIGYIYPYNG GTGYNQKFKSKATITADESTNTAYMELSSLRSEDTAVYYCARGRPAMDYWGQGTLV TVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHT CPPCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGGQPENNYK TTPPVLDSDGSFFLYSKLTVDKSRWQQGNVFSCSVMHEALHNHYTQKSLSLSPG |
| Complete $V_L$ domain (SeqID 4) | DIQMTQSPSSLSASVGDRVTITCRASESVDNYGISFMNWFQQKPGKAPKLLIYAAS NQGSGVPSRFSGSGSGTDFTLTISSLQPDDFATYYCQQSKEVPWTFGQGTKVEIKR TVAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC |

EXAMPLE 6

Conjugation of AGC0700 with Chelator AGC0015

The naked antibody AGC0700 was conjugated (coupled) with the water soluble chelator AGC0015 (12). AGC0015 was prepared in a solution of metal-free. The chelator (12) is presented below:

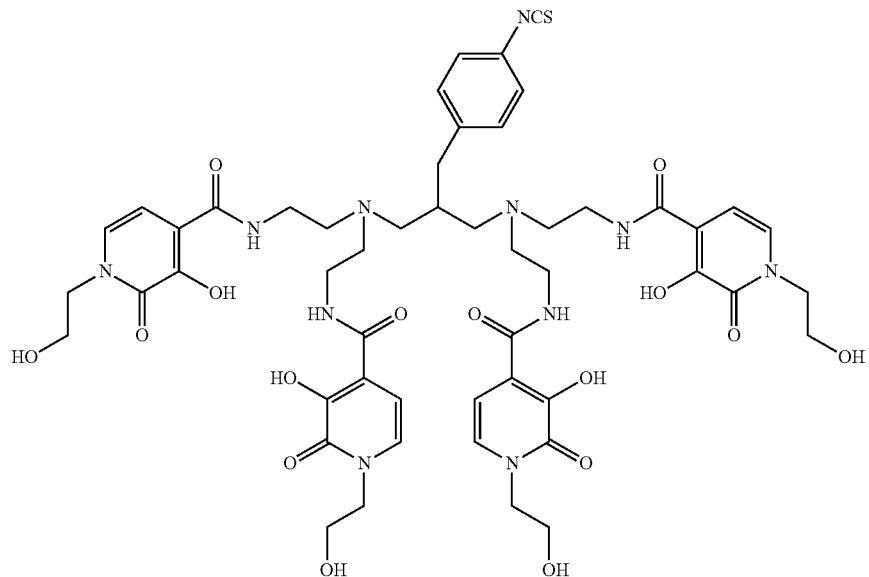

12

Figure 1:
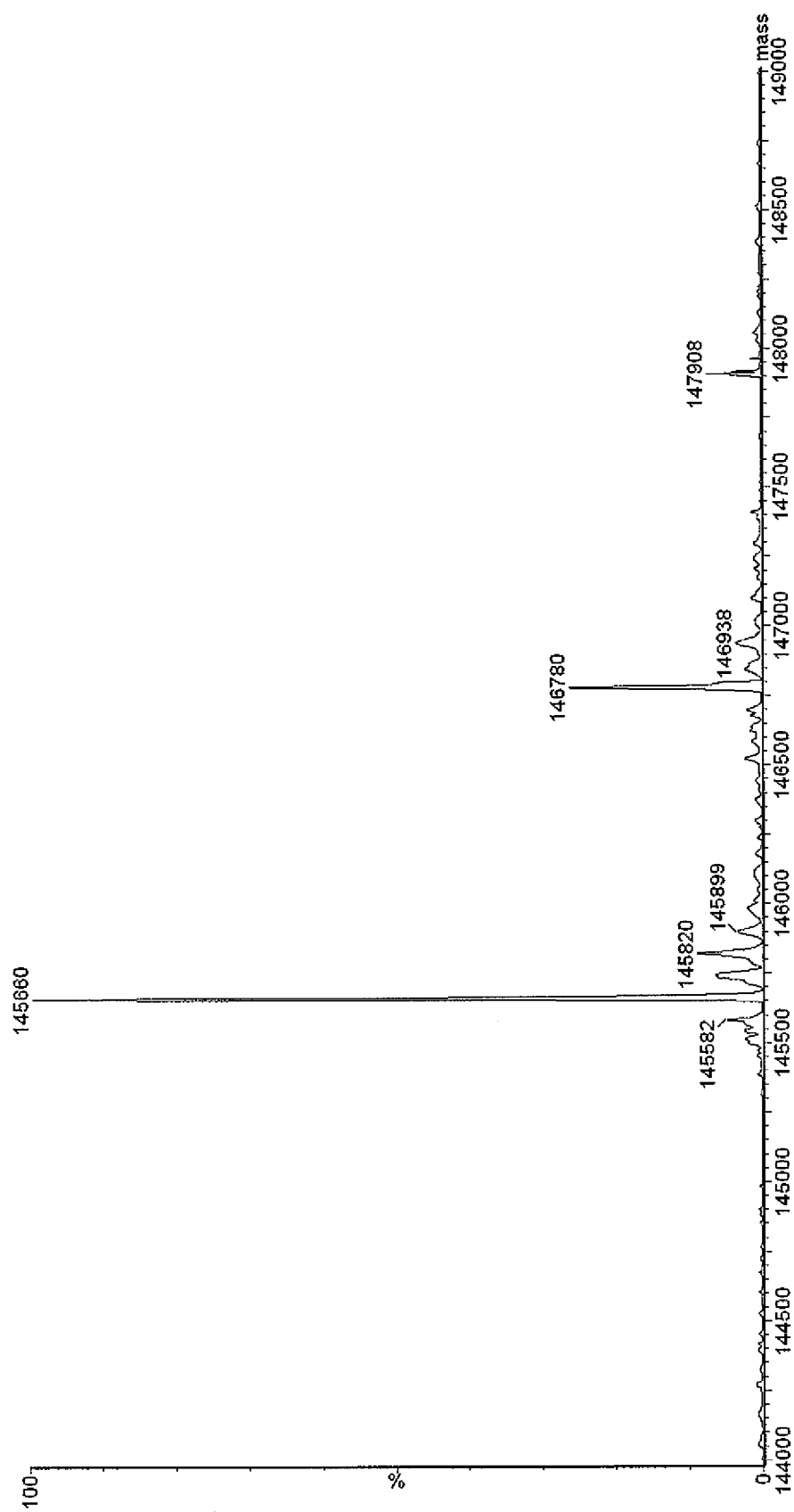
FIG. 1: Mass spectrum AGC0715 (above), showing the distribution of unconjugated mAb, and mAb conjugated with 1 or 2 chelators, respectively. The average chelator-to-antibody ratio (CAR) is approximately 0.3.

The reaction was performed in a 1:1 (v/v) mixture of PBS, mixed with 70 mM borate buffer at a pH of 8.5. A nominal molar chelator to antibody ratio of 1.3:1 was used and the reaction was incubated for 20 hours at 21° C. At the end of reaction time the antibodies were separated from free chelator by size exclusion chromatography on an ÄKTA Purifier (Amersham), using HiLoad Superdex 200 16/600 PG column (GE Healthcare; part.no. 29-9893-35) and 50 mM histidine buffer of pH 6.0 as a mobile phase. The final chelator-antibody-ratio (CAR) of purified conjugates was determined by size exclusion chromatography-mass spectrometry (SEC-MS) analysis. Samples were enzymatically deglycosylated using recombinant EndoS (IgGZERO, Genovis, Sweden) prior to LC-MS analysis. Briefly, the chromatography was done on an Acquity UPLC system (Waters) and the column was a TSK Gel Super SW 3000, 2.0×300 mm, 4 μm particles (part no. 21485) maintained at room temperature. The mobile phase was: 50% acetonitrile in water, 0.1% (v/v) trifluoroacetic acid (isocratic elution). The injection volume was up to 15 μL and the LC flow rate was 75 μL/min or 50 μl/min, for intact conjugates and reduced conjugates, respectively. The total SEC run time was 16 minutes. The Xevo QTOF mass spectrometer (Waters) was equipped with an electrospray ionization (ESI) source. The ion source was operated in positive ion mode and the scan range was 2000-4000 Da. Multiply charged ions were transformed to singly charged species by using the Maximum Entropy software. The mass spectrometer was previously calibrated with sodium iodide in the given mass range. Intact conjugate gave one peak the SEC-MS chromatogram, containing all conjugate species (chelators 0-n). Representative results of a CAR-determination are presented in FIG. 1. The m/z signals corresponding to naked mAb (no chelator), conjugate containing one chelator, and conjugate containing two chelators was identified. Reduced deglycosylated conjugate separated into the peaks corresponding to heavy chain and light chain with no, one or two chelators attached.

EXAMPLE 7

Chelation of Antibody-Chelator Conjugate AGC0715 with Th-227

Thorium-227 as a 4+ ion was isolated from an actinium-227 generator system. Briefly, Th-227 was selectively retained from a Ac-227 decay mixture in 8 M HNO3 by anion exchange chromatography (negatively charged nitrate complexes are formed with $^{227}$Th4+). After Ac-227, Ra-223 and daughters had been washed from the column, Th-227 was eluted using 12 M HCl. The Th-227 eluate was evaporated to dryness and the residue dissolved in 0.5 M HCl.

The antibody-conjugate AGC0715 was incubated for one hour in histidine buffer, pH 6.0 at 37° C. in the presence of 1 MBq of Th-227 per 0.5 mg antibody. The high molecular fraction containing radio labelled antibody-conjugates was separated from free Th-227 and daughter nuclides by size exclusion chromatography using NAP-5 DNA Grade columns (GE Healthcare). The labelling efficiency was typically 96-98%, including potential losses in the NAP-5 desalting step.

EXAMPLE 8

Binding Studies of AGC0700 and AGC0715 to CD33-Positive Cells by Flowcytometry Binding to CD33-positive HL-60 cells were studied by flow cytometry. The determination of $EC_{50}$ based on the plotted curve gives an approximate value for the affinity. The commercially available mouse anti human CD33 (BD Pharmingen; #555450, 1 mg/mL) was used as a reference antibody for assessment of the affinity, including a setup with a 50:50 mixture with the mAb to be analyzed. This assay was also used to confirm that target binding affinity was not negatively affected by conjugation with the chelator.

HL-60 cells were grown in Iscove's Modified Dulbecco's Medium (IMDM; Invitrogen; #12440-046) in the presence of 20% of fetal bovine serum and penicillin/streptomycin. Approximately 20 mL cell culture was harvested by centrifugation at 4° C. for 5 min at 300 g. Cells were re-suspended in 10 mL PBS, supplemented with 1% of fetal bovine serum (FBS), and pelleted by centrifugation at 4° C. for 5 min at 300 g. Subsequently, 20 µL of the preparation of resuspended cells was diluted 1:500 in Coulter Isoton II Diluent, and counted using a Beckman Coulter Z2 instrument (Beckman Coulter; CA, USA). The preparation was adjusted to a cell density of $3\text{-}4\times10^6$ cells/mL, and 100 µL was transferred to each well in a round or V-shaped bottom 96-well plate (Nunc/Fisher Scientific; NH, USA). Cells were spun down and re-suspended after decantation, which resulted in an approximate volume of 50 µL cell suspension per well.

The mAb or conjugate to be analyzed was prepared fresh form frozen stock by shifting the storage buffer to PBS, kept at 4° C., and used within a few days after preparation. $F(ab)_2'$ Alexa488 conjugated goat anti-human IgG Fc (Jackson Immuno Research; #109-546-170) was used as a secondary antibody reagent for detection of human mAb. The secondary antibody reagent was prepared at 0.015 mg/mL in PBS, supplemented with 0.1% BSA. The mAb stock was diluted in 10-fold dilution steps, starting from 5 mg/mL. An isotype control mAb (trastuzumab) was prepared accordingly. 20 uL from each dilution step of the anti-human CD33 mAb was added to wells containing HL-60 cells. After incubation for 1 h at 4° C. the cells were spun down and washed three times with 200 µl cold PBS, supplemented with 0.1% BSA. A solution containing 4% goat serum was added as a blocking agent, and incubated for 15 minutes. 20 µl from the secondary antibody reagent was subsequently added to each well, before incubation for 30 min at 4° C. in the dark.

Figure 2A:
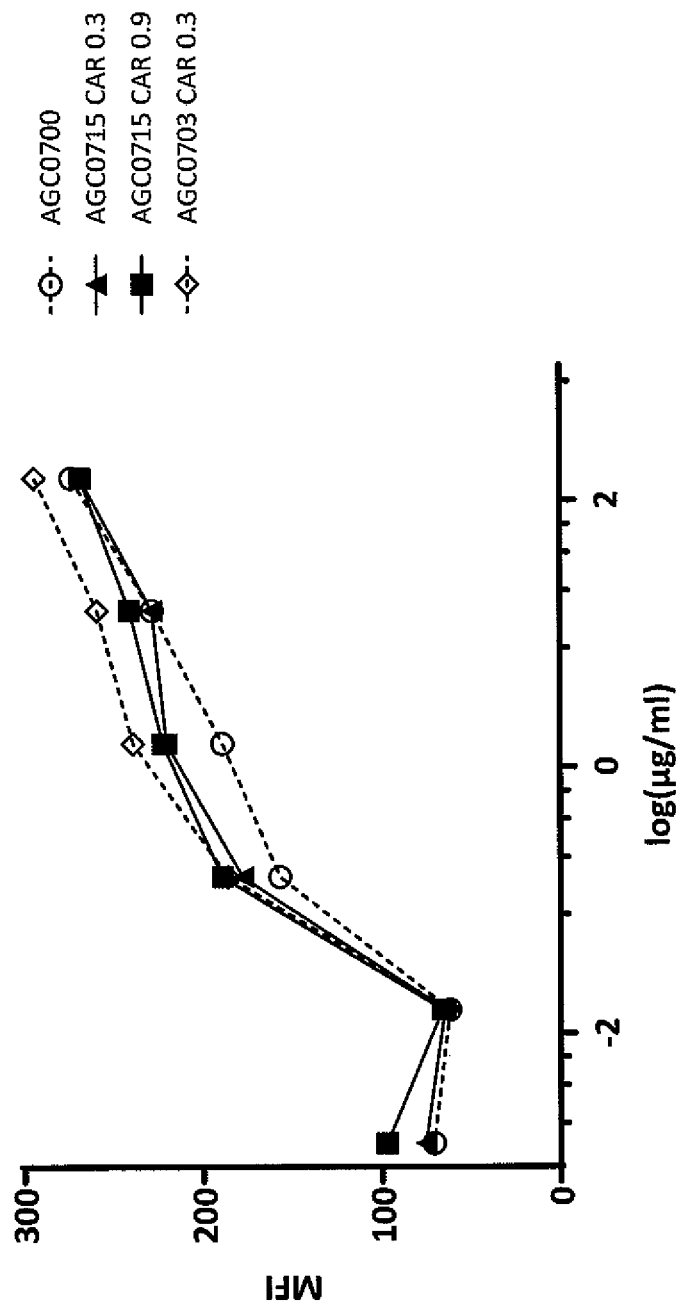
FIG. 2 A-B. Binding of AGC0700, and AGC0715, analysed by flowcytometry on CD33-positive HL-60 cells. Antibodies were detected using goat anti-human Fc, Alexa488 conjugated secondary antibodies, and mean fluorescence intensity (MFI) was plotted against primary antibody concentration in μg/ml. AC0103 (Herceptin) was used as an isotype-like control. AGC0715 at different chelator-to-antibody (CAR) ratios was compared with unconjugated AGC700 (A). In a control experiment the AGC700 was mixed with a 50:50 mixture a reference mouse anti-human CD33 antibody (B).
Figure 2B:
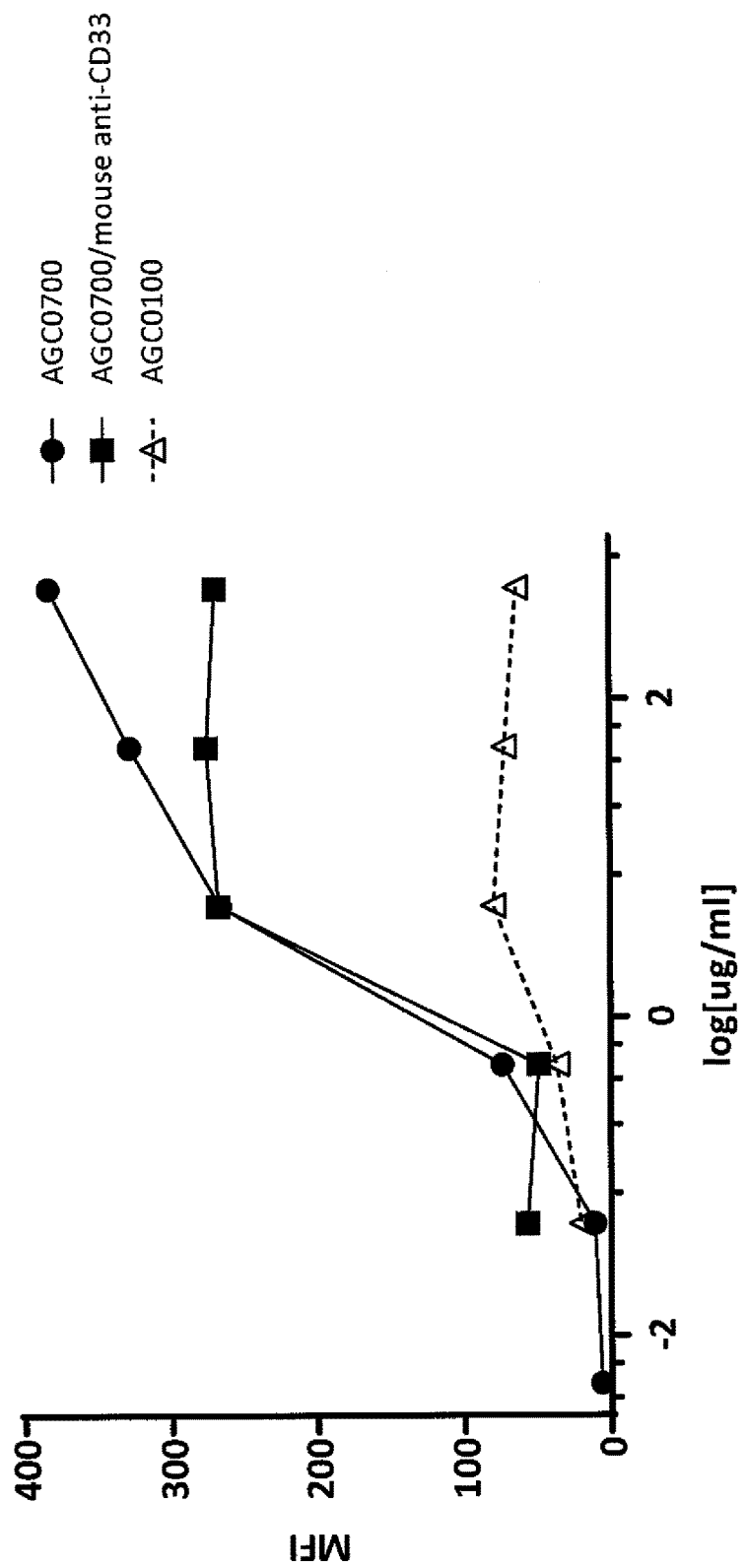

The cells were washed twice, as described above, and re-suspended in 200 µL PBS, supplemented with 0.1% BSA. All samples were analysed in 96-well round or conical bottom plates. Fluorescent signals were recorded on a Beckham Coulter Cell lab Quant SC flow cytometer (Beckman Coulter; CA, USA). Median values were exported to an Excel graph sheet and plotted against the concentration. Data were fitted using the "one-site specific" binding model in Graph Pad Prism (PrismSoftware; CA, USA) (FIG. 2A-B).

The negative control with secondary but no primary antibody showed low background, mean fluorescent intensity (MFI) values of approximately 5 (1-2% of the high positive values).

The binding affinities of the conjugate AGC0715 was comparable to the non-conjugated AGC0700. Thus, conjugation did not result in reduced binding affinity (FIG. 2A). The commercial mouse anti-human CD33 reference mAb binds with lower affinity than AGC0700 in a 50:50 mixture of the two antibodies, resulting in about 0.7-fold less antibody bound (FIG. 2B).

EXAMPLE 9

Internalisation of AGC0715

The extent of internalisation of a radioimmunoconjugate after attachment to outer cell membrane is one factor determining the cell killing potency. Internalization into HL-60 cells of the radioimmunoconjugate AGC0715-Th-227 and the negative control trastuzumab-AC0015-Th-227 was studied.

The conjugated mAbs were labelled in parallel according to the procedure described in Example 5, to a specific activity of about 20 Bq/ug. Wells containing 200 000 cells in 500 µL growth medium (Iscove's Modified Dulbecco's Medium (IMDM; Invitrogen; #12440-046) supplemented with 20% of fetal bovine serum and penicillin/streptomycin) were added equal amounts of radioimmunoconjugate, corresponding to 12 kBq.

Figure 3:
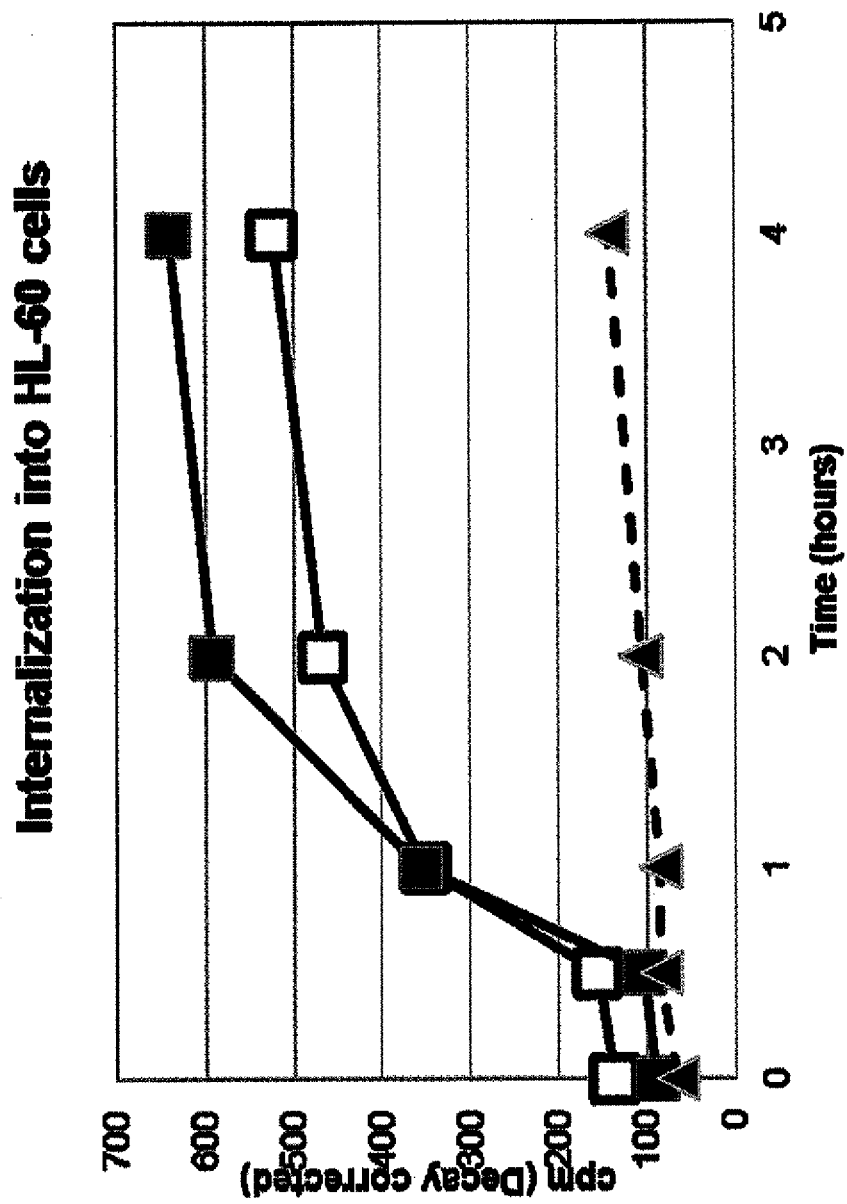
FIG. 3: Internalization of AGC0715-Th-227 (filled squares) and AGC0703-Th-227 (open squares), and the negative control trastuzumab-AC0015-Th-227 (triangles).

Samples of cells were harvested after 0, 30, 60, 120, and 240 minutes incubation time at 37° C. and 5% $CO_2$. After harvest the cells were washed with glycine pH 2.5, 0.9% NaCl to remove membrane bound antibody-conjugates. Analysis by flow cytometry showed that no membrane bound antibody remained after a 2-4 minutes acid wash. Internalisation was measured on cell pellets on a gamma counter (Wizard) for 60 seconds and the measured counts per minute were plotted against time (FIG. 3).

EXAMPLE 10

Th-227-Induced Cell Cytotoxicity by AGC0715-Th-227

In vitro cell cytotoxicity was investigated in CD33 positive HL-60 cells. AGC0715 and the control trastuzumab conjugated AGC0015 were used to chelate Th-227 to a specific activity of 44 kBq/µg. HL-60 cells were grown at 37° C. with 5% $CO_2$, and split 1:5 three times a week. The day before the assay the culture medium (Iscove's Modified Dulbecco's Medium (IMDM) with 20% FBS and 1% Penicillin/Streptomycin) was replaced by new medium and the volume adjusted to give 400 000 cells per mL.

About, 1 600 000 cell (4 mL) were added to each well in a 6 well plate. The plate was incubated until next day for addition of labelled mAb, or culture medium. After adding labelled mAb, or culture medium, the plate was incubated for 4 additional hours. In one experiment AGC0715 or trastuzumab-AGC0015 was added to each well to a final concentration of 3 nM. In another experiment the final concentration was 0.3 nM.

Following incubation, the cells were washed twice in culture medium, and the ATP in the supernatant and in the pellet was measured. The cells were then split 1:2 and incubated in culture medium at 37° C. with 5% $CO_2$. The same procedure, but with only one wash, was repeated at days 2, 4, and 7. A quantification of ATP was used as a measure of cell viability at different sample times (CellTiter-Glo Luminescent cell viability assay from Promega), resulting in the growth curves shown in FIGS. 4A and B.

The HL-60 tumour cell binding AGC0715-Th-227 resulted in cellular toxicity, in contrast to the trastuzumab construct, not binding to HL60 cells. The loss of viability from day 4 to day 7 in the culture medium control is believed to be due to a too long interval between media replacement.

EXAMPLE 11

Effective Tumour Targeting by AGC0715 in a Human Xenograft Model

Female NMRI nude mice were xenografted with cells from the human HL-60 tumour cell line. HL-60 cells are derived from a patient with acute promyelocytic leukemia, and express CD33 according to Sutherland et al (3). This cell line has been proven to be tumourigenic when inoculated subcutaneously into nude mice (4). 54 female NMRI nude mice (Taconic, Europe) were used in the study.

The animals were allowed an acclimation period of at least 5 days before entering the study and were at an age of 4 weeks before tumour inoculation. The mice had an approximated body weight of 20 grams at the start of the study. Animals were kept in individually ventilated cages (IVC, Scanbur) with HEPA filtered air and had ad libitum access to "Rat and mouse nr.3 Breeding" diet (Scanbur BK) and water acidified by addition of HCl to a molar concentration of 1 mM (pH 3.0). HL-60 cells (ATCC/United Kingdom; Catalog Number CCL-240) were grown and prepared for subcutaneous inoculation in IMDM (Invitrogen; #12440-046) in presence of 20% FCS and penicillin/streptomycin. Stocks were made at passage number four (P4) and frozen down for storage in liquid nitrogen at 3×107 cells/vial in the culture media containing 5% DMSO.

On the day of inoculation, the cells were thawed quickly in a 37° C. water bath (approx. 2 min), washed and resuspended in PBS, supplemented with 2% FCS (centrifugation at 1200 rpm for 10 min). Cells were mixed thoroughly every time cells before aspiration into the dosing syringe. A volume of 0.1 mL of cell suspension was injected s.c. at the back using a fine bore needle (25G) while the animals were under light-gas anaesthesia ($N_2O$). Animals were returned to their cages and the tumours were allowed to grow for 15 days. Dosing of test article (0.1 mL) was performed as an intravenous bolus via the tail vein.

Animals were randomized into 3 groups (n=6) after 21 days of tumour growth, and injected with the test compound $^{227}$Th-AGC0715 at a dose of 15 kBq/animal. Animals were euthanized at predetermined time points post injection, and blood, muscle, femur, kidneys, lung, liver, stomach, small intestine, large intestine and tumour were collected. Tissues and blood samples were weighed, and the radioactivity in each sample was measured using gamma spectroscopy (HPGe15p or HPGe50p germanium detectors).

The measured radioactivity (Bq) was related to the radioactivity measured in 10% injection standard samples, and the percentage of Th-227 and Ra-223 were calculated and presented as % ID or % ID per gram of tissue. Two animals were excluded from the analysis because of large tumours compared to the rest of the group, as retrospective analysis showed an inverse relation between tumour uptake and tumour size (data not shown). The data confirm specific tumour uptake of the AGC0715-Th-227. Previous studies have shown that non-specific retention of a mAb in the tumour due to vascular leakage is washing out over time and do not exceed a few % ID/g at day 7 (data not shown).

Figure 5:
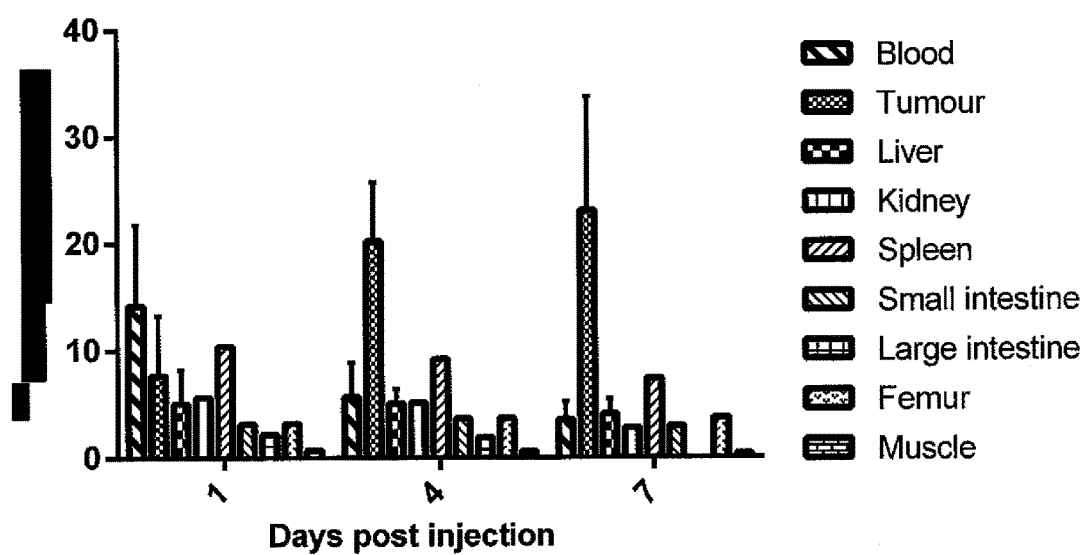
FIG. 5: Biodistribution of $^{227}$Th-AGC0715 in HL-60 tumour bearing nude mice. Data shows high tumour uptake at day 7 p.i. (23±10.7% ID/g).

The results of the biodistribution study are presented in the FIG. 5. The data demonstrate expected tumour targeting. Build-up of radioactivity was seen in the tumour, but in no normal tissue.

EXAMPLE 12

In Vivo Efficacy of AGC0715-Th-227 in Xenografted Mice

Cell preparation and xenografting of female NMRI nude mice are done as described in Example 9. The animals are allowed an acclimation period of at least 5 days before entering the study and are at an age of 4 weeks before tumour inoculation. The mice have an approximated body weight of approximately 20 grams at the start of the study. Animals are kept in individually ventilated cages (IVC, Scanbur) with HEPA filtered air and have ad libitum access to "Rat and mouse nr.3 Breeding" diet (Scanbur BK) and water acidified by addition of HCl to a molar concentration of 1 mM (pH 3.0). Mice will be inoculated with tumour cells about 10 days before dosing in order to have mice with average size of tumours in the range from 75-150 mm3. Animals are randomized into 4 treatment groups and 3 control groups (n=10/group).

Mice in the treatment groups are injected into the tail vein with 100 µL containing 75 kBq/mL, 150 kBq/mL, 225 kBq/mL or 300 kBq/mL AGC0715-Th-227, to achieve 250, 500, 750 or 1000 kBq/kg body weight (b.w.). The mice in the control groups are administered either with vehicle only (buffer), non-radioactive antibody (AGC0715) or trastuzumab-Th-227, labelled to a specific activity of 500 kBq/kg (isotype control).

Appearance of tumours will carefully be monitored, and the tumours will be scored (if not large enough to be measured) or measured thrice a week according to the following scheme:

| Scores: | |
|---|---|
| 0 | Tumour cannot be detected |
| 1 | Tumour is palpable |
| 2 | Just before measurements will be possible |

| Marks: | |
|---|---|
| R | Red |
| W | Signs of wound tissue |
| N | Necrosis |
| B | Blue |

Tumour diameters will be measured in two dimensions using a digital caliper and the volume will be estimated by the following formula: L×W×½ W (Length×Width×½ Width). Measurements/observations will start at day 0, i.e. the day of inoculation. Measurements of tumour volumes will be three times a week, Monday, Wednesday and Friday. Body weights will be recorded once a week. The data will be presented in figures and descriptive statistics will be conducted.

The mice will be terminated following maximal tumour size of 15 mm diameter. This diameter is equal to a volume of 1688 mm$^3$ when assuming a spherical form. No adverse clinical sigs is expected in this study. In case of observations of adverse clinical signs, these will be recorded as note to files.

After the study different treatment groups are compared by Caplan Meyer survival curve. Treatment-induced tumour growth is also plotted and growth delays are calculated after nonlinear regression of mean growth versus time and compared using Student T Test.

The data of the efficacy study are expected to be similar to previously published efficacy data obtained after administration of the monoclonal antibodies trastuzumab and rituximab labelled with thorium-227.

EXAMPLE 13

Generation of the Anti-CD22 Monoclonal Antibody (AGC1100)

The sequence of the monoclonal antibody (mAb) hLL2, also called epratuzumab, here denoted AGC1100, was constructed as described in (1). The mAb used in the current examples was produced by Immunomedics Inc, New Jersey, USA. Production of this mAb could for example be done in Chinese hamster ovarian suspension (CHO-S) cells, transfected with a plasmid encoding the genes encoding the light and the heavy chain. First stable clones would be selected for using standard procedures. Following approximately 14 days in a single-use bioreactor, the monoclonal antibody may be harvested after filtration of the supernatant. AGC1100 would be further purified by protein A affinity chromatography (MabSelect SuRe, Atoll, Weingarten/Germany), followed by an ion exchange step. A third purification step based on electrostatic and hydrophobicity could be used to remove aggregates and potentially remaining impurities. The identity of AGC1100 would be confirmed by isoelectric focusing, SDS-PAGE analysis, N-terminal sequencing and LC/MS analysis. Sample purity would be further analyzed by size-exclusion chromatography (SEC).

Known sequences of CD22 binding antibodies (murine and humanised) include the following (where CDRs are bold and predicted contact regions outside of CDRs are underlined):

Light Chain:
(SeqID5)
DIQLTQSPSSLAVSAGENVT<u>MSC</u>KSSQSVLYSANHKNYLA<u>W</u>YQQKPGQSP <u>KLLIY</u>WASTRES<u>G</u>VPDRFTGS<u>G</u>S<u>GTD</u>F<u>T</u>LTISRVQVEDLAIYY<u>C</u>HQYLSS
WT<u>F</u>GGGTKLEIKR (SeqID8)
<u>QVQL</u>QQSGAEVKKPGSSVKVSCKASG<u>YTFT</u>SYWLH<u>W</u>VRQAPGQGLE<u>WIGY</u>

INPRNDYTEYNQNFKD<u>KA</u>TITADESTNTAY<u>MELSS</u>LR<u>SED</u>TAFYFCA<u>R</u>RD

ITTFY<u>W</u>GQGTTVTVSS (SeqID9)
<u>QVQL</u>VQSGAEVKKPGSSVKVSCKASG<u>YTFT</u>SYWLH<u>W</u>VRQAPGQGLE<u>WIGY</u>

INPRNDYTEYNQNFKD<u>KA</u>TITADESTNTAY<u>MELSS</u>LR<u>SED</u>TAFYFCA<u>R</u>RD

ITTFY<u>W</u>GQGTTVTVSS

REFERENCES
(1) Leung, Goldenberg, Dion, Pellegrini, Shevitz, Shih, and Hansen. Molecular Immunology 32: 1413-27, 1995.

EXAMPLE 14
Conjugation of AGC1100 with the Chelator AGC0015

The antibody AGC1100 was conjugated with the water soluble chelator AGC0015. (12) The conjugation reaction was performed in a 1:1 (v/v) mixture of PBS mixed with 70 mM borate buffer pH 8.5. The chelator, AGC0015 is as shown below:

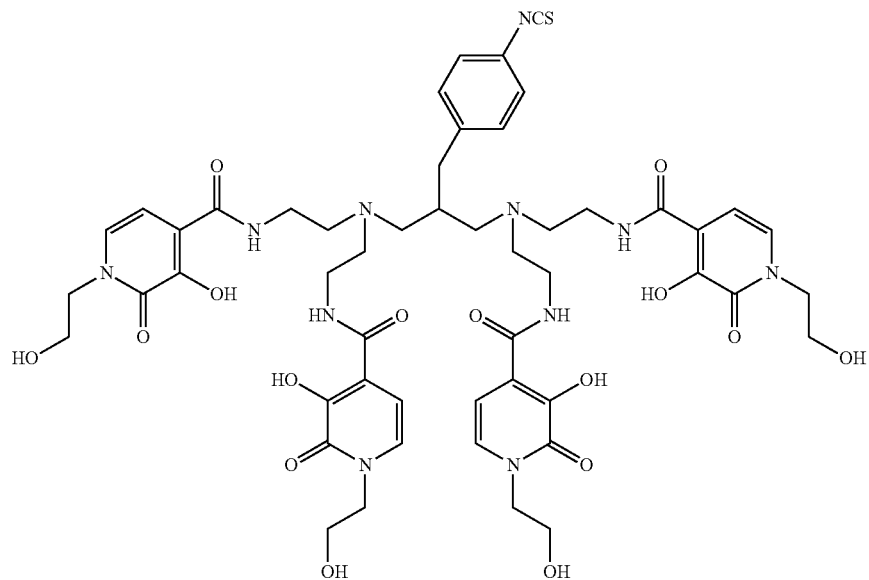

12

-continued
(SeqID6)
DIQLTQSPSSLASAAVEDRT<u>MSC</u>KSSQSVLYSANHKNYLA<u>W</u>YQQKPGQKA <u>KLLIY</u>WASTRES<u>G</u>VPSRFSGS<u>G</u>S<u>GTD</u>F<u>T</u>FTISSLQPEDIATYY<u>C</u>HQYLSS

WT<u>F</u>GGGTKLEIKR

Heavy Chain:
(SeqID7)
<u>QVQL</u>QESGAELSKPGASVKMSCKASG<u>YTFT</u>SYWLH<u>W</u>IKQRPGQGLE<u>WIGY</u>

INPRNDYTEYNQNFKD<u>KA</u>TLTA<u>D</u>KSSSTAY<u>MQLSS</u>LT<u>SED</u>SAVYYCA<u>R</u>RD

ITTFY<u>W</u>GQGTTLTVSS

Figure 6A:
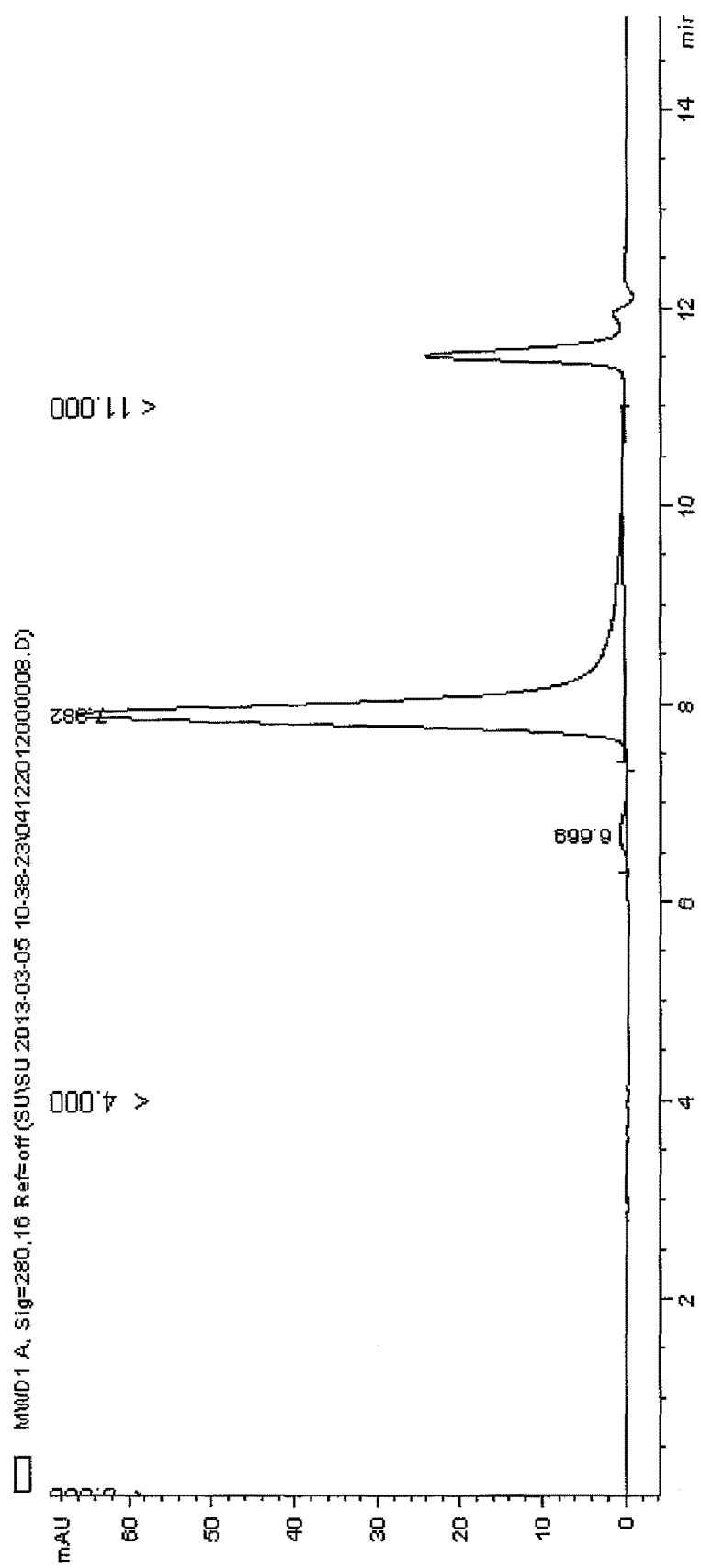
FIG. 6: SEC-UV chromatogram of AGC1115 at 280 nm (A) and 335 nm (B). The average chelator-to-antibody ratio (CAR) is approximately 0.9.
Figure 6B:
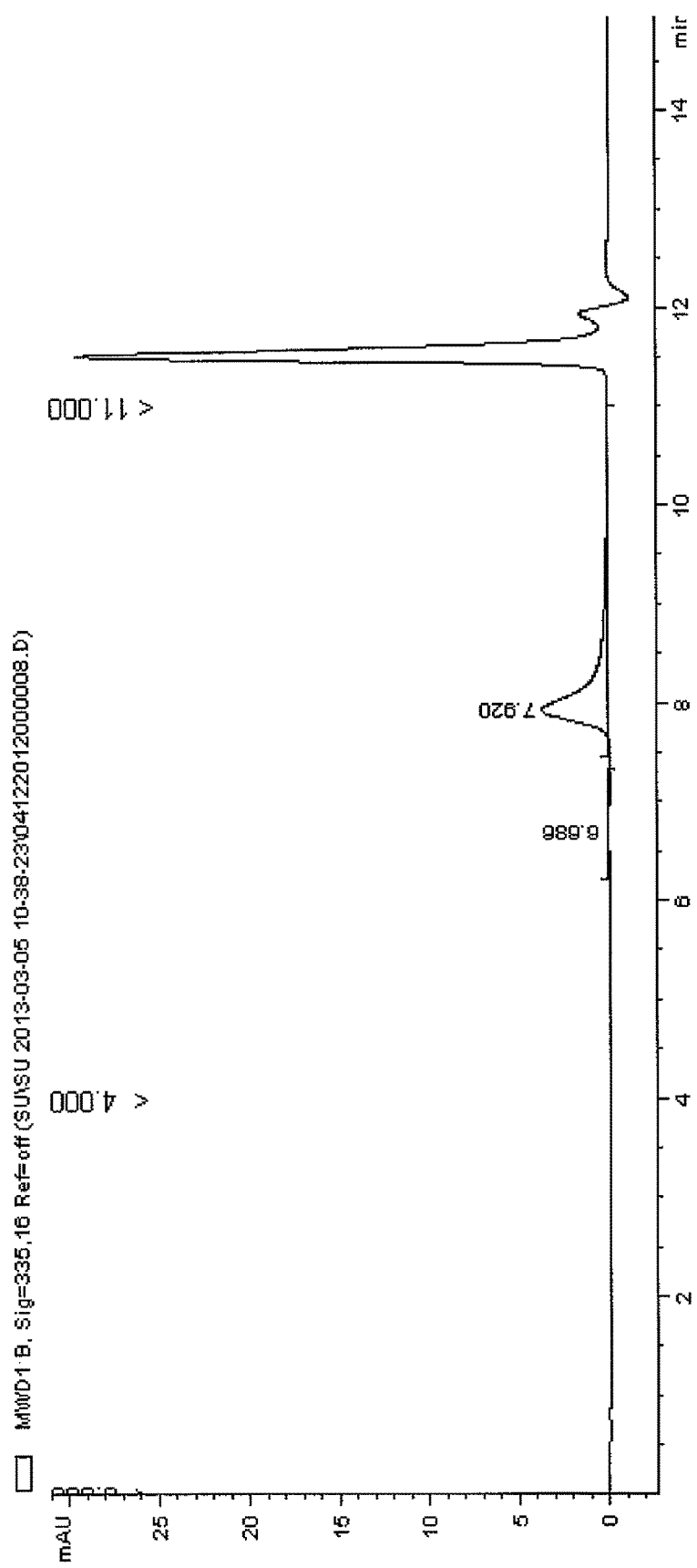

The chelator, AGC0015 (12 above), was dissolved in metal-free water before it was added to the conjugation reaction. A nominal molar chelator to antibody ratio of 1.3:1 was used and the reaction was incubated for 22 hours at 21° C. At the end of reaction time the antibody fraction was separated from free chelator by size exclusion chromatography on an ÄKTA Purifier (GE Healthcare), using a HiLoad Superdex 200 16/600 PG column (GE Healthcare; code.no. 28-9893-35) and 0.9% NaCl 100 mM citrate buffer pH 5.5 as mobile phase. The final chelator-antibody-ratio (CAR) of purified conjugate was determined by HPLC size exclusion chromatography-UV (SEC-UV) analysis. The CAR determination was done on an Agilent 1200 series HPLC system (Agilent Technologies), column TSKgel SuperSW 3000, 4.6×300 mm, 4 μm particles (Tosoh Bioscience, part no. 18675) maintained at room temperature and mobile phase 300 mM NaCl 200 mM ammonium acetate pH 6.8 (isocratic elution) with a total run time of 15 minutes. The injection volume was 5 µl and the LC flow rate was 0.35 ml/min. The UV signals were monitored at 280 and 335 nm, corresponding to mAb and chelator absorbance maximum, respectively. Representative results of a CAR-determination are presented in FIG. 6.

EXAMPLE 15

Chelation of Antibody/Chelator Conjugate AGC1115 with Th-227

Thorium-227 ($^{227}$Th) as a 4+ ion was isolated from an actinium-227 ($^{227}$Ac) generator system. $^{227}$Th was selectively retained from a $^{227}$Ac decay mixture in 8 M HNO$_3$ by anion exchange chromatography, where negatively charged nitrate complexes are formed with $^{227}$Th$^{4+}$. $^{227}$Ac and daughter nuclides were washed off the column and $^{227}$Th was eluted in 12 M HCl. The $^{227}$Th-eluate was evaporated to dryness and the residue dissolved in 0.5 M HCl.

In the chelation reaction the antibody-conjugate AGC1115 was incubated for 15 minutes in 0.9% NaCl 100 mM citrate buffer, pH 5.5 at 21° C./room temperature in the presence of 1 MBq $^{227}$Th per 0.5 mg antibody conjugate. The high molecular fraction containing radio labelled antibody-conjugate was separated from free $^{227}$Th and daughter nuclides by size exclusion chromatography using NAP-5 DNA Grade columns (GE Healthcare). The labelling efficiency was typically 96-98%, including potential loss in the NAP-5 desalting step.

EXAMPLE 16

Binding Analysis of AGC1115 and AGC1100 to CD22-Positive Raji Cells by Flow Cytometry Binding of AGC1115 and AGC1100 (anti-human CD22, Immunomedics; hLL2, #1003164, 10 mg/ml) to CD22-positive Raji cells (ATCC, #CCL-86) was analysed by flow cytometry. The EC$_{50}$ value determined from the fitted curve was used for comparison of the antibody versus the antibody conjugate binding potency. This analysis was used to confirm that antibody conjugate binding potency to CD22 was unaffected by the conjugation procedure.

Raji cells were grown in RPMI 1640 (PAA; #E15-840) in the presence of 10% fetal bovine serum (FBS) and 1% penicillin/streptomycin. For the flow cytometry analysis 50 ml cell culture was harvested by centrifugation at 4° C. for 5 min at 340×g. Cells were resuspended and washed twice in 10 ml PBS, supplemented with 1% FBS, and pelleted by centrifugation at 4° C. for 5 min at 340×g. Subsequently, 20 µl of the preparation of resuspended cells was diluted 1:500 in Coulter Isoton II Diluent, and counted using Beckman Coulter Z2 instrumentation (Beckman Coulter; CA, USA). The preparation was adjusted to a cell density of 1×10$^6$ cells/ml and 100 µL was transferred to each well in a V-shaped bottom 96-well plate (Nunc/Fisher Scientific; NH, USA). Cells were spun down and re-suspended after decantation, which resulted in an approximate volume of 50 µl cell suspension per well.

AGC1115 and AGC1100 was diluted to 50 µg/ml and titrated in twelve points in 3-fold dilution steps. An isotype control antibody (trastuzumab) was prepared accordingly. 100 µl from each dilution of the antibody was added to the wells containing Raji cells. After incubation for 1.5 h at 4° C., the cells were spun down and washed twice with 200 µl cold PBS, supplemented with 1% FBS. PE conjugated mouse anti-human IgG Fc (BioLegend; #409304) was used as a secondary antibody reagent for detection of human mAb. The secondary antibody reagent was prepared at 1 µg/ml in PBS, supplemented with 1% FBS. 100 µl from the secondary antibody reagent was subsequently added to each well, before incubation for 1 h at 4° C. in the dark. The cells were washed twice, as described above, and resuspended in 200 µl PBS, supplemented with 1% FBS. All samples were analysed in a V-shaped bottom 96-well plate. Fluorescent signal was recorded on a Beckman Coulter Cell Lab Quanta SC MPL flow cytometer (Beckman Coulter; CA, USA). Median values (MFI) were exported to an Excel sheet and plotted against the concentration ([nM]).

Data was fitted using the "log(agonist) vs. response—Variable slope (four parameters)" binding model in Graph Pad Prism (PrismSoftware; CA, USA) and the EC$_{50}$ values was calculated from the fit (FIG. 7). Direct staining of the Raji cells with secondary antibody showed low background, MFI values of approximately 1 (0.5-1% of the AGC1115 MFI values).

The calculated EC$_{50}$ values of the fitted titration curves of AGC1100 and AGC1115 were 9 nM and 6 nM, respectively, and indicated that the binding potency of the conjugate AGC1115 was comparable to AGC1100.

EXAMPLE 17

Th-227-Induced Cell Cytotoxicity by AGC1115-Th-227

In vitro cell cytotoxicity was investigated in CD22 positive Ramos cells (see Example 6). AGC1115 and the control trastuzumab conjugated with AGC0015 were used to chelate Th-227 to a specific activity of 44 kBq/µg.

Ramos cells were grown at 37° C. with 5% CO$_2$, and split 1:5 three times a week. The day before the assay the culture medium (Iscove's Modified Dulbecco's Medium (IMDM) with 20% FBS and 1% Penicillin/Streptomycin) was replaced by new medium and the volume adjusted to give 400 000 cells per mL. About, 1 600 000 cell (4 mL) were added to each well in a 6 well plate. The plate was incubated until next day for addition of labelled mAb, or culture medium.

After adding labelled mAb, or culture medium, the plate was incubated for 4 more hours. In the experiment AGC1115 or trastuzumab-AGC0015 was added to each well to a final concentration of 3 nM. Following incubation, the cells were washed twice in culture medium, and the ATP in the supernatant and in the pellet was measured. The cells were then split 1:2 and incubated in culture medium at 37° C. with 5% CO$_2$. The same procedure, but with only one wash, was repeated at days 3, 5 and 7.

A quantification of ATP was used as a measure of cell viability at different sample times (CellTiter-Glo Luminescent cell viability assay from Promega), resulting in the curves shown in FIG. 8. The Ramos cell binding AGC1115-Th-227 resulted in cellular toxicity, in contrast to the Th-227 labelled control construct, not binding to Ramos cells.

EXAMPLE 18

Acid Derivative

Making an acid derivative of the water soluble chelator enabling alternative coupling chemistries.

This example shows the successful synthesis of an acid derivative. This derivative of the chelator enables, for example, formation of an amide bond with an epsilon amine of the tumour targeting protein.

The present example shows the synthesis of the soluble chelator and starts out from substance 11 (Example 2). 43 mg (~0.04 mmol) of substance 11 was dissolved in 4 mL DMSO, 4 mL acetonitrile, and 30 µL NEt₃. 6 mg of succinic anhydride was added (0.06 mmol). LC/MS analysis of the reaction mix after 22 hours reaction at room temperature showed that substance 15 had formed. Some contaminant diacylated side product was formed. Adding the anhydride in portions should minimize the ester formation and improve molar yield of product 14. HPLC analysis of the resulting reaction mixture is shown in FIG. 9.

phosphate buffer, pH7.4), containing 2 mM tris(2-chloroethyl)phosphine (TCEP) to hinder disulphide formation. One ml of the affibody fusion protein solution was mixed with 0.985 ml 0.14 M borate buffer, and the pH confirmed to be about 8.4. 15 µL of 1 mg/ml solution of iodoacetamide (Sigma 1149-5 g) was added and the reaction mix incubated for 1 hour at room temperature.

Before conjugation, the 4 ml solution containing sulfhydryl blocked Affibody fusion protein was concentrated to 0.5 mL using Amicon spin filters, and excess reactants removed on a NAP5 desalting column (GE Healthcare, lot#83892624) equilibrated with borate buffer. The eluted 1

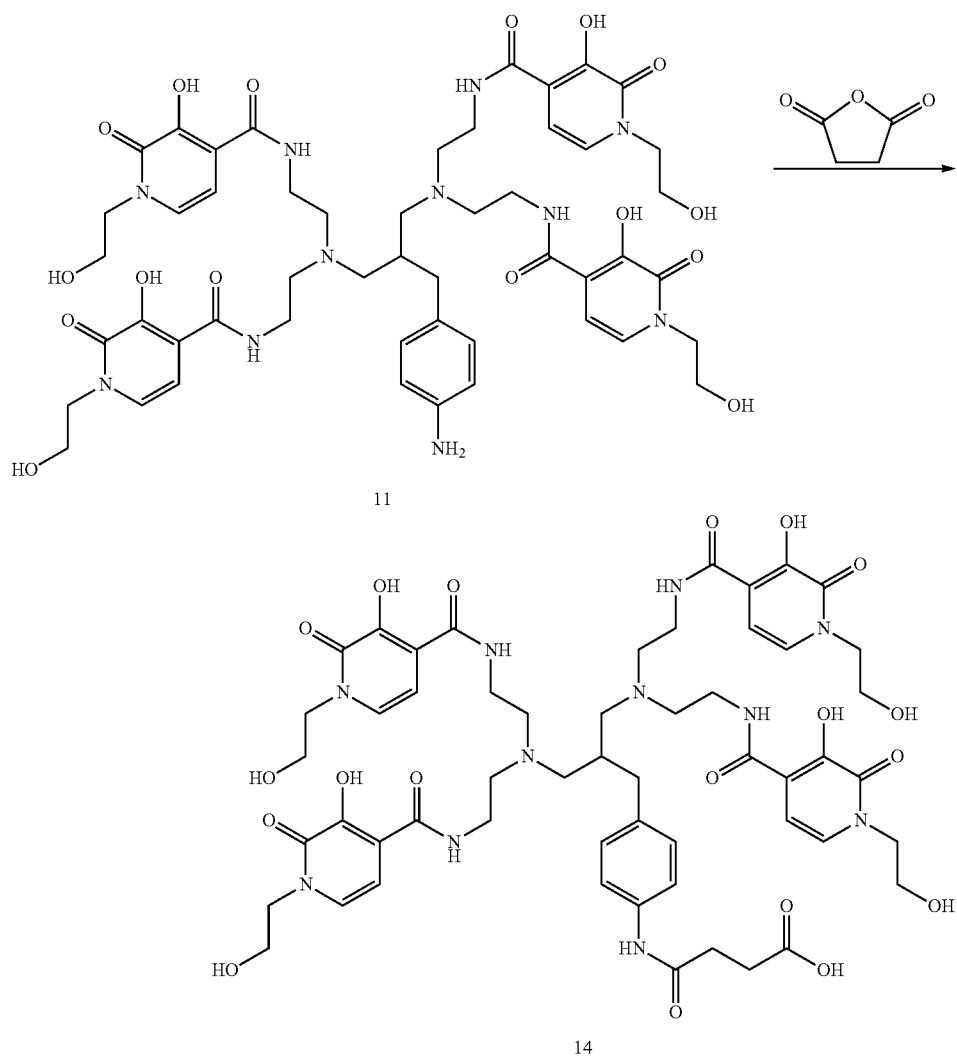

EXAMPLE 19

Conjugation of AGC0003 and AGC0015 to a Small Protein

Since lysine coupling was going to be used, the free cysteine of the Affibody fusion protein was chemically blocked before conjugation with the chelators. The Affibody fusion protein PEP9237 (SeqID 10) made in *E. coli* by essentially as described by Tolmachev et al. (1), was dissolved to 1.32 mg/ml in PBS (Biochrom L1825; 0.9% NaCl, mL high molecular weight fraction was spilt in two parts for reacting with either AGC0003 or AGC0015.

The chelator AGC0003 (8.3 µL DMF (Sigma 227056, lot# STBB4668)—13 below-containing 10 mg/ml) was added to a vial containing 0.5 mL sulfhydryl blocked Affibody fusion protein. The chelator AGC0015 (9.3 µL H₂O containing 10 mg/ml) was added to a separate vial containing 0.5 mL sulfhydryl blocked Affibody fusion protein. Both vials containing chelator protein reaction mixtures were incubated over night at 30° C. The resulting clear solution was buffer exchanged to PBS using a NAP5 column.

SeqID10:
AEAKYAKEMRNAYWEIALLPNLTNQQKRAFIRKLYDDPSQSSELL
SEAKKLNDSQAPSGSGSLAEAKEAANAELDCYGVSDFYKRLIDKA
KTVEGVEALKDAILAALPG 13 (AG0003)

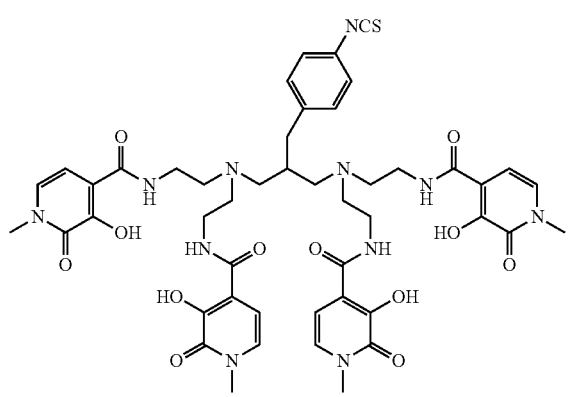

EXAMPLE 20

Solubility Analyses of the Small Protein Conjugates with AGC0003 and AGC0015

The clear PBS solution of the two Affibody fusion protein chelator conjugates produced in Example 19 were frozen at −20° C., before thawing. A distinct milky precipitation was seen with the solution containing AGC0003 conjugate, but not with the in AGC0015 conjugate. The precipitation was more visible after cooling down to on ice.

The clear solution from either reaction was analysed by FPLC-SEC, to investigate possible aggregates (FIG. 10). More than 50% the AGC0003 conjugate was found to be in the aggregated state, whereas a minor fraction of the AGC0015 conjugate (sees as a shoulder in the chromatogram) was in the aggregated state. The integrated area under the curve showed much less total protein recovered for AGC0203 (AGC0003 conjugate) than for AGC0215 (AUC: 166 and 409 mAU*mL respectively)

Next, the protein to chelator ratio was investigated by LC/MS analysis. The unconjugated Affibody fusion protein (AGC200) was included as a control. During LC absorption was monitored at 280 and 335 nm (chelator absorbs at approx. 335 nm), showing that chelator was present in the two conjugate solutions but not in the AGC200 preparation (FIG. 11). With the AGC0003 conjugate (AGC0203), the MS analysis showed both unconjugated fusion protein and protein conjugate with one chelator, whereas with the AGC0015 conjugate (AGC0215), the MS analysis showed unconjugated fusion protein and protein conjugate with one and two chelators (FIG. 12). This indicates that AGC0203 with more than one chelator has precipitated.

REFERENCES

Tolmachev, Orlova, Pehrson, Galli, Baastrup, Andersson, Sandström, Rosik, Carlsson, Lundqvist, Wennborg, Nilsson. Radionuclide therapy of HER2-positive microxenografts using a 177Lu-Labeled HER2-specific Affibody molecule. Cancer Res. 67: 2773-82, 2007.

---

The invention claimed is:

1. A tissue-targeting complex comprising
a tissue targeting moiety selected from the group consisting of a monoclonal or polyclonal antibody, an antibody fragment, a construct of said antibody or fragment, and an antibody mimetic,
an octadentate hydroxypyridinone-containing ligand comprising four chelating 3,2-HOPO moieties of formula I

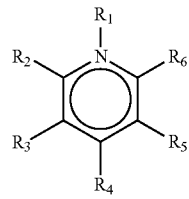

I wherein $R_1$ is a hydroxyalkyl moiety; groups $R_4$ to $R_6$ are each H, $R_3$ is OH, and $R_2$ is =O,
and the 4+ion of the alpha-emitting thorium radionuclide $^{227}$Th.

2. The complex as claimed in claim 1 wherein the N-substituents on each of the four HOPO groups are each independently chosen from $HOCH_2$—, $HOCH_2CH_2$—, HO—$CH_2CH_2CH_2$—, HO—$CH(CH_3)CH_2$—, HO—$CH_2CH_2CH_2CH_2$—, HO—$CH(CH_3)CH_2CH_2$—, HO—$CH(CH_2CH_3)CH_2$—, HO—$C(CH_3)_2CH_2$—, HO—$CH(CH_3)CH(CH_3)$—and $HOCH_2CH(CH_2CH_3)$—.

3. The complex as claimed in claim 1 comprising a ligand moiety of formula VI:

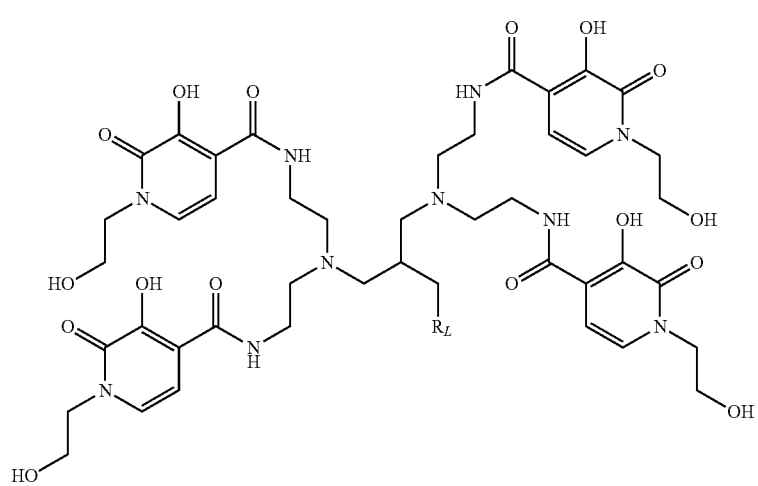

VI wherein $R_L$ is a linker moiety for attachment of the ligand moiety to the tissue targeting moiety.

4. A complex as claimed in claim 1 wherein the antibody fragment (is a Fab, a $F(ab')_2$, a Fab', or a scFv.

5. A method of treatment of a human or non-human animal in need thereof comprising administration of
a tissue targeting moiety selected from the group consisting of a monoclonal or polyclonal antibody, an antibody fragment, a construct of said antibody or fragment, and an antibody mimetic, an octadentate hydroxypyridinone-containing ligand comprising four chelating 3,2-HOPO moieties of formula I

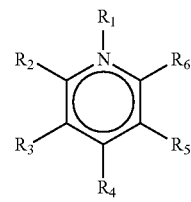

wherein $R_1$ is a hydroxyalkyl moiety; groups $R_4$ to $R_6$ are each H, $R_3$ is OH, and $R_2$ is =O,
and the 4+ion of the alpha-emitting thorium radionuclide $^{227}$Th.

6. The method as claimed in claim 5 for the treatment of hyperplastic or neoplastic disease, a carcinoma, a sarcoma, a myeloma, leukemia, a lymphoma or a mixed type cancer.

7. A pharmaceutical composition comprising a tissue-targeting complex as defined in claim 1 together with at least one pharmaceutical carrier or excipient.

8. A kit for use in a method according to claim 5, said kit comprising a tissue targeting moiety, conjugated or conjugatable to an octadentate hydroxypyridinone-containing ligand comprising four 3,2-HOPO moieties, where all four HOPO moieties are substituted at the N-position with a hydroxyalkyl solubilising group, said kit including the alpha-emitting thorium radionuclide $^{227}$Th.

9. A method of formation of a tissue-targeting complex, said method comprising coupling a tissue targeting moiety to an octadentate hydroxypyridinone-containing ligand in aqueous solution, the complex comprising four 3,2-HOPO moieties and the ion of an alpha-emitting thorium radionuclide, where all four HOPO moieties are substituted at the N-position with a hydroxyalkyl solubilising group.

10. The method of claim 9 comprising preparing a first aqueous solution of octadentate hydroxypyridinone-containing ligand and a second aqueous solution of said tissue targeting moiety and contacting said first and said second aqueous solutions.

11. The method of claim 10 wherein said contacting is conducted at below 40° C.

12. The method of claim 10 wherein said contacting is conducted in the substantial absence of any organic solvent.

13. The method of claim 9 wherein said coupling yields an amide, ester, ether or amine bond between the ligand moiety and the targeting moiety.

14. The method of claim 13 wherein said amide or ester linkage is formed by means of at least one activated ester group.

15. The method as claimed in claim 5, wherein said antibody fragment is a Fab, a F(ab')$_2$, a Fab', or a scFv.

16. The method of claim 13, wherein said amide or ester linkage is formed by means a N-hydroxy maleimide, carbodiimide, or azodicarboxylate coupling reagent.

* * * * *